(12) United States Patent
Stratton et al.

(10) Patent No.: US 7,947,819 B2
(45) Date of Patent: May 24, 2011

(54) B-RAF POLYNUCLEOTIDES

(75) Inventors: Mike Stratton, Hinxton (GB); Andy Futreal, Hinxton (GB); Richard Wooster, Hinxton (GB); Richard Malcolm Marais, London (GB); Chris Marshall, London (GB)

(73) Assignee: The Wellcome Trust, London (GB)

( * ) Notice: Subject to any disclaimer, the term of this patent is extended or adjusted under 35 U.S.C. 154(b) by 360 days.

(21) Appl. No.: 10/873,057

(22) Filed: Jun. 21, 2004

(65) Prior Publication Data

US 2005/0186584 A1    Aug. 25, 2005

Related U.S. Application Data

(63) Continuation of application No. PCT/GB02/05891, filed on Dec. 23, 2002.

(60) Provisional application No. 60/344,684, filed on Dec. 24, 2001.

(30) Foreign Application Priority Data

Dec. 21, 2001    (GB) ................................. 0130796.6

(51) Int. Cl.
  *C07H 21/04*    (2006.01)
(52) U.S. Cl. ..................................... 536/23.1; 536/23.2
(58) Field of Classification Search .................. None
See application file for complete search history.

(56) References Cited

FOREIGN PATENT DOCUMENTS

| WO | WO-9740184 A | 10/1997 |
|---|---|---|
| WO | WO-9822103 A | 5/1998 |
| WO | WO-9847077 A | 10/1998 |
| WO | WO-9902167 A | 1/1999 |
| WO | WO-9932106 A | 7/1999 |
| WO | WO 01/13111 A2 | 2/2001 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Kramer et al, Enzymatic amplification of DNA by PCR. Unit 15.1 In: Current Protocols in Molecular Biology 2001. Abstract.*
NCBI GenBank Accession No. NP_003424.*
Tommerup et al, Isolation and fine mapping of 16 novel human zinc finger-encoding cDNAs identify putative candidate genes for developmental and malignant disorders. Genomics. May 20, 1995;27(2):259-64.*
Duby et al, UNIT 6.4 Using Synthetic Oligonucleotides as Probes. In: Current Protocols in Molecular Biology (1993) pp. 6.4.1-6.4.10.*
SCORE USPTO in house printout; SEQ ID No. 2 annotating residues 1796-1797, filed Feb. 19, 2009.*
USPTO in house alignment SID2vsG14757867NP_004333. Performed Apr. 8, 2009.*
USPTO in house alignment SID1vsG14757868NP_004324. Performed Apr. 8, 2009.*
USPTO in house translation of SEQ ID No. 2. Performed Apr. 8, 2009.*
A_Geneseq_200812 database Acc#AEN28392 from Edgerton US2005108791, priority date Dec. 4, 2001. Alignment with SEQ ID No. 2.*
Peyssonnaux, C. et al., (2001), "The Raf/MEK/ERK pathway: new concepts of activation", *Biology of the Cell*, 93:53-62.
Papin, et al., (1996), "Identification of signalling proteins interacting with B-Raf in the yeast two-hybrid system", *Oncogene*, May 16;12(10):2213-21.
Barnier, J.V. et al., (1995), "The Mouse B-*rai* Gene Encodes Multiple Protein Isoforms with Tissue-specific Expression", *The Journal of Biological Chemistry*, 270(40):23381-23389.
Pritchard, C.A. et al., (1995), "Conditionally Oncogenic Forms of the A-Raf and B-Raf Protein Kinases Display Different Biological and Biochemical Properties in NIH 3T3 Cells", *Molecular and Cellular Biology*, 15(11):6430-6442.
Eychène, A. et al., (1992), "Chromosomal assignment of two human B-*raf*(R*mil*) proto-oncogene loci: B-*raf*-1 encoding the p94$^{Braf}$ R*mil* and B-*raf*-2, a processed pseudogene", *Oncogene*, 7:1657-1660.
Huebner, K. et al., (1986), "Actively transcribed genes in the *raf* oncogene group, located on the X chromosome in mouse and human", *Proc. Natl. Acad. Sci. USA*, 83:3934-3938.
MacNicol, et al; "Disruption of the 14-3-3 Binding Site within the B-Raf Kinase Domain Uncouples Catalytic Activity from PC12 Cell Differentiation"; (2000); *The Journal of Biological Chemistry*; 275(6): 3803-3809.
Okada, et al.; "The Strength of Interaction at the Raf Cysteine-Rich Domain Is a Critical Determinant of Response of Raf to Ras Family Small GTPases"; (1999); *Molecular and Cellular Biology*; 19(9): 6057-6064.
Guan, et al.; "Negative Regulation of the Serine/Threonine Kinase B-Raf by Akt"; (2000); *The Journal of Biological Chemistry*; 275(35): 27354-27359.
Ikawa, et al.; "B-raf, a New Member of the raf Family, Is Activated by DNA Rearrangement"; (1988); *Molecular and Cellular Biology*; 8(6): 2651-2654.
Sithanandam, et al.; "Complete coding sequence of human B-raf cDNA and detection of B-raf protein kinase with isozyme specific antibodies"; (1990); *Oncogene*; 5: 1775-1780.
International Preliminary Examination Report dated Aug. 12, 2004.
Zhang et al, "Activation of B-Raf Kinase Requires Phosphorylation of the Conserved Residues Thr598 and Ser601" EMBO J., 2000, vol. 19, p. 5429-5439.
Database Medline Online! US National Library of Medicine (NLM), Bethesda, MD, US; Apr. 27, 1993 Sithanandam, G.et al: "Human B-raf mRNA, complete cds" retrieved from US National Library of Medicine (NLM), Bethesda, M, accession No. M95712, Database accession No. gi: 179532 XP002249539.

(Continued)

*Primary Examiner* — Sheridan Swope
(74) *Attorney, Agent, or Firm* — Edwards Angell Palmer & Dodge LLP; Kathleen Williams; Elbert Chiang

(57) ABSTRACT

The invention relates to mutations in B-Raf gene products. The mutations described are identified in human tumors of natural origin. These mutations are associated with cancerous phenotypes and can be used as a basis for the diagnosis of cancer, cancerous cells or a predisposition to cancer in human subjects, and the development of anti-cancer therapeutics.

3 Claims, 8 Drawing Sheets

OTHER PUBLICATIONS

Database Medline Online1 US National Library of Medicine (NLM), Bethesda, MD, US; Apr. 9, 1996 Ikawa et al : "Human B-raf oncogene mRNA, 3' end" retrieved from US National Library of Medicine (NLM), Bethesda, M, accession No. M21001, Database accession No. gi: 179534 XP002249540.

Database EMBL Online EBI Sequence ID. 42, Sep. 12, 2000. Monia "Antisense oligonucleotide modulation of B-raf gene expression" Accession No. AR085564.

Database EMBL Online EBI: Human B-raf mRNA, complete cds, Jun. 15, 1992. Sithanandam et al, Complete coding sequence of a human B-raf cDNA and detection fo B-raf protein kinase with isozyme specific antibodies, accession No. HSBRAF3 XP002256147.

Whitehouse et al, Progress in Forensic Genetics, XX, XX, 2000, vol. 8, No. 1193, p. 412-415 XP000981339.

Papin et al, Journal of Biological Chemistry, 1998, vol. 273, No. 38, p. 24939-24947 XP002256145.

Alessi et al, Methods of Enzymology, 1995, vol. 225, p. 279-290 XP008022766.

Sebolt-Leopold, Oncogene, 2000, vol. 10, No. 56, p. 6594-6599.

Yeung et al, Molecular and Cellular Biology, 2000, vol. 20, No. 9, p. 3079-3085.

Lyons et al, Endocrine-related Cancer, 2001, vol. 8, No. 3, p. 219-225 XP008022717.

Monia et al, Proceedings of the National Academy of Sciences of the United States of America, 1996, vol. 93, No. 26, p. 15481-15484 XP002073792.

Gayle et al., The Journal of Biological Chemistry, "Identificatioin of Regions in Interleukin-1α Important for Activity" 1993; vol. 268, No. 29, p. 22105-11.

Whisstock, et al.; Quarterly Reviews of Biophysics, "Prediction of Protein Function from Protein Sequence and Structure"; 2003, vol, 36, No. 3, p. 307-340.

Kramer et al. "Current Protocols in Molecular Biology", 2001, Abstract.

N. Tommerup, et al.; Genomics, Isolation and Fine Mapping of 16 Novel Human Zinc Finger-Encoding cDNAs Identify Putative Candidate Genes for Developmental and Malignant Disorders; 1995, vol. 27, No. 2, p. 259-264.

Muslin, et al., Molecular and Cellular Biology, vol. 13, No. I 7, "Raf-1 Protein Kinase Is Important for Progesterone-Induced Xenopus Oocyte Maturation and Acts Downstream of mos"; Jul. 1993, p. 4197-4202.

MacNicol, et al. Journal of Biological Chemistry; "Nerve Growth Factor-stimulated B-Raf Catalytic Activity Is Refractory to Inhibition by cAMP-dependent Protein Kinase" vol. 274, No. 19, Issue of May 7, 1999, p. 13193-13197.

GenBank #NM_004324; p. 1-3, Jul. 14, 2008.

* cited by examiner

WM-266.4 cells

Colo 829 cells

Cell cycle analysis

PARP cleavage

SEQUENCE LISTING

```
<160> NUMBER OF SEQ ID NOS: 2

<210> SEQ ID NO 1
<211> LENGTH: 765
<212> TYPE: PRT
<213> ORGANISM: Homo sapiens

<400> SEQUENCE: 1

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Arg Pro
                20                  25                  30

Ala Ala Ser Ser Ala Ala Asp Pro Ala Ile Pro Glu Glu Val Trp Asn
            35                  40                  45

Ile Lys Gln Met Ile Lys Leu Thr Gln Glu His Ile Glu Ala Leu Leu
        50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Met Asp Thr Val Thr Ser Ser Ser Ser Ser Ser Leu Ser
        115                 120                 125

Val Leu Pro Ser Ser Leu Ser Val Phe Gln Asn Pro Thr Asp Val Ala
    130                 135                 140
```

-continued

```
Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Ala Leu Thr Ser Gly Ser Ser Pro Ser Ala Pro
305                 310                 315                 320

Ala Ser Asp Ser Ile Gly Pro Gln Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
    370                 375                 380

Gln Gly Phe Arg Gly Asp Gly Gly Ser Thr Thr Gly Leu Ser Ala Thr
385                 390                 395                 400

Pro Pro Ala Ser Leu Pro Gly Ser Leu Thr Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
        435                 440                 445

Trp Glu Ile Pro Asp Gly Gln Ile Thr Val Gly Gln Arg Ile Gly Ser
    450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
```

```
                        565                 570                 575
Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
            595                 600                 605

Phe Glu Gln Leu Ser Gly Ser Ile Leu Trp Met Ala Pro Glu Val Ile
            610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
            675                 680                 685

Lys Arg Leu Met Ala Glu Cys Leu Lys Lys Lys Arg Asp Glu Arg Pro
            690                 695                 700

Leu Phe Pro Gln Ile Leu Ala Ser Ile Glu Leu Leu Ala Arg Ser Leu
705                 710                 715                 720

Pro Lys Ile His Arg Ser Ala Ser Glu Pro Ser Leu Asn Arg Ala Gly
                725                 730                 735

Phe Gln Thr Glu Asp Phe Ser Leu Tyr Ala Cys Ala Ser Pro Lys Thr
            740                 745                 750

Pro Ile Gln Ala Gly Gly Tyr Gly Ala Phe Pro Val His
            755                 760                 765

<210> SEQ ID NO 2
<211> LENGTH: 2510
<212> TYPE: DNA
<213> ORGANISM: Homo sapiens

<400> SEQUENCE: 2
cgcctcccgg ccccctcccc gcccgacagc ggccgctcgg gccccggctc tcggttataa      60
gatggcggcg ctgagcggtg gcggtggtgg cggcgcggag ccgggccagg ctctgttcaa     120
cggggacatg gagcccgagg ccggcgccgg ccggcccgcg gcctcttcgg ctgcggaccc     180
tgccattccg gaggaggtgt ggaatatcaa acaaatgatt aagttgacac aggaacatat     240
agaggcccta ttggacaaat tggtgggga gcataatcca ccatcaatat atctggaggc     300
ctatgaagaa taccaccagc agctagatgc actccaacaa agagaacaac agttattgga     360
atctctgggg aacggaactg attttttctgt ttctagctct gcatcaatgg ataccgttac     420
atcttcttcc tcttctagcc tttcagtgct accttcatct ctttcagttt ttcaaaatcc     480
cacagatgtg gcacggagca accccaagtc accacaaaaa cctatcgtta gagtcttcct     540
gcccaacaaa cagaggacag tggtacctgc aaggtgtgga gttacagtcc gagacagtct     600
aaagaaagca ctgatgatga gaggtctaat cccagagtgc tgtgctgttt acagaattca     660
ggatggagag aagaaaccaa ttggttggga cactgatatt tcctggctta ctggagaaga     720
attgcatgtg gaagtgttgg agaatgttcc acttacaaca cacaactttg tacgaaaaac     780
gttttttcacc ttagcatttt gtgactttttg tcgaaagctg cttttccagg gtttccgctg     840
tcaaacatgt ggttataaat ttcaccagcg ttgtagtaca aagttccac tgatgtgtgt     900
taattatgac caacttgatt tgctgttttgt ctccaagttc tttgaacacc acccaatacc     960
acaggaagag gcgtccttag cagagactgc cctaacatct ggatcatccc cttccgcacc    1020
```

```
cgcctcggac tctattgggc cccaaattct caccagtccg tctccttcaa aatccattcc    1080
aattccacag cccttccgac cagcagatga agatcatcga aatcaatttg ggcaacgaga    1140
ccgatcctca tcagctccca atgtgcatat aaacacaata gaacctgtca atattgatga    1200
cttgattaga gaccaaggat ttcgtggtga tggaggatca accacaggtt tgtctgctac    1260 ccccccctgcc tcattacctg gctcactaac taacgtgaaa gccttacaga aatctccagg    1320
acctcagcga gaaggaagt catcttcatc ctcagaagac aggaatcgaa tgaaaacact    1380
tggtagacgg gactcgagtg atgattggga gattcctgat gggcagatta cagtgggaca    1440
aagaattgga tctggatcat ttggaacagt ctacaaggga aagtggcatg gtgatgtggc    1500
agtgaaaatg ttgaatgtga cagcacctac acctcagcag ttacaagcct tcaaaaatga    1560
agtaggagta ctcaggaaaa cacgacatgt gaatatccta ctcttcatgg gctattccac    1620
aaagccacaa ctggctattg ttacccagtg gtgtgagggc tccagcttgt atcaccatct    1680
ccatatcatt gagaccaaat ttgagatgat caaacttata gatattgcac gacagactgc    1740
acagggcatg gattacttac acgccaagtc aatcatccac agagacctca agagtaataa    1800
tatatttctt catgaagacc tcacagtaaa aataggtgat tttggtctag ctacagtgaa    1860
atctcgatgg agtgggtccc atcagtttga acagttgtct ggatccattt tgtggatggc    1920
accagaagtc atcagaatgc aagataaaaa tccatacagc tttcagtcag atgtatatgc    1980
atttgggatt gttctgtatg aattgatgac tggacagtta ccttattcaa acatcaacaa    2040
cagggaccag ataattttta tggtgggacg aggatacctg tctccagatc tcagtaaggt    2100
acggagtaac tgtccaaaag ccatgaagag attaatggca gagtgcctca aaagaaaag    2160 agatgagaga ccactctttc cccaaattct cgcctctatt gagctgctgg cccgctcatt    2220
gccaaaaatt caccgcagtg catcagaacc ctccttgaat cgggctggtt tccaaacaga    2280
ggattttagt ctatatgctt gtgcttctcc aaaaacaccc atccaggcag ggggatatgg    2340 tcgtttcct gtccactgaa acaaatgagt gagagagttc aggagagtag caacaaaagg    2400
aaaataaatg aacatatgtt tgcttatatg ttaaattgaa taaaatactc tcttttttt    2460 taaggtggaa aaaaaaaaa aaaaaaaaa aaaaaaaaa aaaaaaccc    2510
```

US 7,947,819 B2

B-RAF POLYNUCLEOTIDES

Related Applications

This application is a Continuation of PCT/GB02/05891 filed Dec. 23, 2002 which claims priority under 35 U.S.C. §119 to U. S. Provisional Application Ser. No. 60/344,684, filed 24 Dec. 2001 and to GB 0130796.6 filed 21 Dec. 2001, the entirety of which is incorporated herein by reference.

FIELD OF THE INVENTION

The present invention relates to cancer-specific mutants of B-raf genes and uses thereof in the detection of abnormal cells and cancer. Moreover, the invention describes methods for the diagnosis of cancer, the detection of cancerous cells in subjects and the development of therapeutic agents for the treatment of cancer.

INTRODUCTION

Cancer can develop in any tissue of any organ at any age. Most cancers detected at an early stage are potentially curable; thus, the ability to screen patients for early signs of cancer, and thus allowing for early intervention, is highly desirable (See, for instance, the Merck Manual of Diagnosis and Therapy (1992)16th ed., Merck & Co).

Cancerous cells display unregulated growth, lack of differentiation, and ability to invade local tissues and, metastasize. Thus cancer cells are unlike normal cells, and are potentially identifiable by not only their phenotypic traits, but also by their biochemical and molecular biological characteristics. Such characteristics are in turn dictated by changes in cancerous cells which occur at the genetic level in a subset of cellular genes known as oncogenes, which directly or indirectly control cell growth and differentiation.

The Raf oncogene family includes three highly conserved genes termed A-, B-and C-raf (also called raf-1). C-Raf, the best characterised member of the raf family, is the cellular homologue of v-raf the transforming gene of the murine sarcoma virus 3611. The viral raf oncogene encodes a protein that lacks the amino-terminal sequences of the normal Raf protein. These amino-terminal sequences are crucial for the regulation of RAF serine/threonine-protein kinase activity, and their deletion or replacement results in constitutive activity of the oncogene-encoded RAF protein. This unregulated activity promotes cell proliferation, resulting in cell transformation. DNA from a few tumours has been alleged to contain a transforming activity detectable by DNA transfection of NIH/3T3 cells, identified as derived from truncated C-raf-1. However, these results are likely to be transfection artefacts as the same mutations have not been found in the tumours from which the transforming DNA was derived. Mutations created artificially in the C-raf gene, when introduced into cells in vitro can induce transformation.

The B-raf gene is the human homologue of the avian c-Rmil protooncogene encoding a 94-kD serine/threonine kinase detected in avian cells. This protein contains amino-terminal sequences not found in other proteins of the mil/raf gene family. These sequences are encoded by 3 exons in the avian genome. Eychene et al. (1992) Oncogene 7:1657-1660 reported that these 3 exons are conserved in the human B-raf gene and that they encode an amino acid sequence similar to that of the avian gene. They identified 2 human B-raf loci: B-raf 1, which was mapped to 7q34 by fluorescence in situ hybridisation and shown to encode the functional gene product, and B-raf 2, an inactive processed pseudogene located on Xq13.

By screening a mouse cDNA library with a v-raf oncogene probe, Huebner et al. (1986) Proc. Nat. Acad. Sci. 83: 3934-3938 isolated a transforming raf-related cDNA, A-raf, that represented a gene distinct from raf1. The single A-raf locus of the mouse and the A-raf1 locus of man are actively transcribed in several mouse and human cell lines. The complete 606-amino acid sequence of the human A-raf1 oncogene has been deduced from the 2,453-nucleotide sequence of the cDNA. The A-raf gene is X-linked.

A known mechanism for the conversion of proto-oncogenes to oncogenes is the appearance of single mutation is in the DNA sequence, known as point mutations, which result in a change in the amino acid sequence of the encoded polypeptide. For example, ras oncogenes are not present in normal cells, but their proto-oncogene counterparts are present in all cells. The wild-type Ras proteins are small GTP-binding proteins that are involved in signal transduction. However, many ras oncogenes from viruses and human tumours have a point mutation in codon number 12: the codon GGC that normally encodes a glycine is changed to GTC, which encodes a valine. Multiple mutations have been documented at this codon, including at least 5. different substitutions which are activating. This single amino acid change prevents the GTPase activity of the Ras protein, and renders Ras constitutively activated, since it remains GTP-bound. The amino acids at positions 13 and 61 are also frequently changed in ras oncogenes from human tumours.

The Raf protein is a serine/threonine kinase that is structurally related to the protein kinase C (PKC) family, and is essential in cell growth and differentiation. Raf proteins are involved in signal transduction in the activation of MAP kinase, which is highly conserved in eukaryotic organisms. MAP kinases (mitogen-activated protein kinases), which include ERK1 and ERK2, directly phosphorylate transcription factors to regulate biological events. MAPKKs (MAP kinase kinases) and MAPKKKs (MAPKK kinases) in turn regulate MAP kinases.

Raf proteins are MAPKKKs and are believed to phosphorylate the MAPKK MEK in vivo in mammalian biological systems. Distinct raf genies encode A-Raf, B-Raf and Raf-1 (also known as c-Raf) in vertebrates (reviewed in Papin et al., 1998, Oncogene 12:2218-2221). The three proteins are not equal in their ability to activate MEK. A-Raf, the less well-characterised member of the family, appears to be a poor MEK activator, its activity being difficult-to measure (Pritchard et al., 1995, Mol. Cell. Biol. 15, 6430-6442). B-Raf and Raf-1 also differ in their ability to activate MEK. While Raf-1 is ubiquitously expressed, B-Raf displays highest levels of expression in neural tissues (Barnier et al., 1995, J. Biol. Chem. 270, 23381-23389). However, B-Raf has been identified as the major MEK activator, even in cells where its expression is barely detectable by western blotting analysis (Catling et al., 1994; Jaiswal et al., 1994; Reuter et al., 1995; Huser et al., 2001; Mikula et al., 2001). Consistently, B-Raf displays higher affinity for MEK-1 and MEK-2 than Raf-1 (Papin et al., 1996; Papin et al., 1998) and is more efficient in phosphorylating the MAPKK MEK.

The upstream activator of B-Raf is the GTPase Ras. A number of Ras isoforms are known to exist in mammals; N-Ras, Ha-Ras, Ki-Ras4A and Ki-Ras4B. Other GTPases of the Ras superfamily may also interact with B-Raf. For example Rap-1, reviewed in Peysonnaux et al., (2001) Biology of the Cell 93:53-62 appears to be a selective activator of B-Raf.

SUMMARY OF THE INVENTION

Point mutations in B-Raf gene products are described herein. The point mutations described are identified in human tumours of natural origin. These point mutations are associated with cancerous phenotypes and can be used as a basis for the diagnosis of cancer, cancerous cells or a predisposition to cancer in human subjects.

Since many of the signalling pathway(s) which are mediated by activation of the kinase activity of B-Raf are involved in control of cell proliferation and oncogenic transformation, it would be desirable to be able to rapidly detect changes in the B-raf gene which can result in an oncogenic character.

Thus, in a first aspect, there is provided a naturally-occurring cancer-associated mutant of a human B-Raf polypeptide comprising one or more mutations.

Preferably, the cancer-associated mutant is isolated from a naturally-occurring primary human tumour.

Preferably, the mutation is in the kinase domain of B-Raf.

The present invention provides several such mutations, which have been found to be associated with a cancerous phenotype in human cancers; and thus establish a link between B-Raf mutations and cancer in vivo.

Preferably, the mutation is a point mutation. Mutations can also include changes such as insertions, deletions or replacements of one or more than one nucleotide, preferably of 2, 3, 4, 5 or 6 nucleotides.

Advantageously, the mutations are located C-terminal to amino acid 300 in B-Raf. Preferred positions are 463, 465, 468, 585, 594, 595, 596 and 599.

In a most preferred embodiment, the mutations are selected from the group consisting of V599E, V599D, G595R, G465V, G465E, G465A, G468A, G468E, E585K, F594L, G595R, L596V, L596R and G463E.

Preferably, the polypeptide is isolated.

The invention moreover encompasses fragments of the polypeptides according to the invention, wherein said fragments include the mutation as described.

In a second aspect, there is provided a nucleic acid encoding a mutant B-Raf polypeptide or fragment thereof in accordance with the present invention. Preferably, the nucleic acid comprises one or more point mutations.

Preferably, the nucleic acid is isolated.

Point mutations in B-raf genes have been detected which show association with tumours. Advantageously, the point mutation occurs at one or more -of positions 1388, 1394, 1403, 1753, 1782, 1783, 1796, 1797, 1787 and 1786 of B-raf. Preferably, the point mutation is G1388T, G1783C, TG1796-97AT, G1394T, G1394A, G1394C, G1403C, G1403A, G1753A, T1782G, G1388A, T1796A, T1787G or C1786G in B-raf. The invention moreover provides the complement of any nucleic acid described above.

In a further embodiment, there is provided a nucleic acid which hybridises specifically to a nucleic acid according to the invention, as described herein. Such a nucleic acid can for example be a primer which directs specific amplification of a mutant B-Raf-encoding nucleic acid according to the invention in a nucleic acid amplification reaction.

In a third aspect, the invention provides a ligand which binds selectively to a mutant B-Raf polypeptide according to the invention.

Such a ligand is advantageously an immunoglobulin, and is preferably an antibody or an antigen-binding fragment thereof.

According to a fourth aspect, there is provided a method for the detection of cellular transformation comprising the steps of:

(a) isolating a sample of cellular material from a subject;

(b) examining nucleic acid material from at least part of one or more B-raf genes in said cellular material; and (c) determining whether such nucleic acid material comprises one or more mutations in a sequence encoding a B-Raf polypeptide.

Advantageously, the mutation is a point mutation.

Advantageously, the mutation occurs at one or more of positions 1388, 1394, 1403, 1753, 1782, 1783, 1796, 1797, 1787 and 1786 of B-raf. Preferably, the point mutation is G1388T, G1783C, TG1796-97AT, G1394T, G1394A, G1394C, G1403C, G1403A, G1753A, T1782G, G1388A, T1796A, T1787G or C1786G in B-raf.

The mutations identified in accordance with the invention are advantageously somatic mutations, which have occurred in somatic tissue and are not transmitted through the germ line. Thus, the invention moreover relates to a method for the detection of cellular transformation, comprising the steps of:

(a) isolating a first sample of cellular material from a tissue of a subject which is suspected to be cancerous, and a second sample of cellular material from a non-cancerous tissue of the same subject;

(b) examining nucleic acid material from at least part of one or more B-raf genes in both said samples of cellular material; and (c) determining whether such nucleic acid material comprises one or more point mutations in a sequence encoding a B-Raf polypeptide; and said mutation being present in the cellular material from the suspected cancerous tissue but not present in the cellular material from the non-cancerous tissue.

The invention moreover provides a method for the detection of cellular transformation, comprising the steps of:

(a) obtaining a sample of cellular material from a subject;

(b) screening said sample with a ligand which binds selectively to a mutant B-Raf polypeptide according to the invention; and (c) detecting one or more mutant B-Raf polypeptides in said sample.

In a still further aspect, the invention relates to a method for identifying one or more compounds having anti-proliferative activity, comprising the steps of:

(a) providing one or more mutant B-Raf polypeptides in accordance with the present invention;

(b) contacting said polypeptide(s) with one or more compounds to be tested; and (c) detecting an interaction between said one or more compounds and said mutant polypeptides.

Preferably, the interaction is a binding interaction.

Moreover, the invention provides an assay for identifying one or more compounds having anti-proliferative activity, comprising the steps of:

(a) providing one or more mutant B-Raf polypeptides in accordance with the present invention;

(b) providing a downstream substrate for the B-Raf polypeptide;

(c) detecting modification of the substrate in presence of the compound(s) to be tested.

B-Raf is a protein kinase, and accordingly substrates therefore are capable of being phosphorylated or dephosphorylated. Preferably, the action of mutant B-Raf on the substrate results in a detectable change therein. Advantageously, the substrate is a further kinase or phosphatase, which in turn modifies a third molecule in which a detectable change occurs.

For example, the substrate may be the kinase MEK. MEK phosphorylation may be detected directly, or, preferably, is detected through activation of MEK to phosphorylate MAP Kinase.

Advantageously, a reference activity of mutant B-Raf on the substrate is established, and the activity in the presence and/or absence of the compound(s) to be tested compared to the reference value. A decrease in the activity of the mutant B-Raf is indicative of a reduction in proliferative activity.

The invention moreover provides a cell-based assay for screening compounds for anti-proliferative activity. In a first embodiment, a the invention provides a 3T3 focus-forming assay comprising the steps of:
  (a) providing a culture of NIH 3T3 cells;
  (b) transfecting said cells with a mutant B-raf nucleic acid in accordance with the invention;
  (c) exposing the cells to one or more compound(s) to be tested; and
  (d) determining the difference in the number of foci formed between transfected cells exposed to said compound(s) to be tested and transfected cells not so exposed.

The cell-based assay is commonly performed using NIH 3T3 cells. However, other cell types, especially fibroblast cells, can be used in such an assay.

Advantageously, a reference focus-forming activity of a mutant B-raf gene on the cells used in the assay is established, and the activity in the presence and/or absence of the compound(s) to be tested compared to the reference value. A decrease in the focus-forming activity of the mutant B-raf gene is indicative of a reduction in proliferative activity and thus of antiproliferative activity in the compound(s) being tested.

Automated methods and apparata for the detection of mutations in accordance with the invention are also provided.

DETAILED DESCRIPTION OF THE INVENTION

Figure 1A:
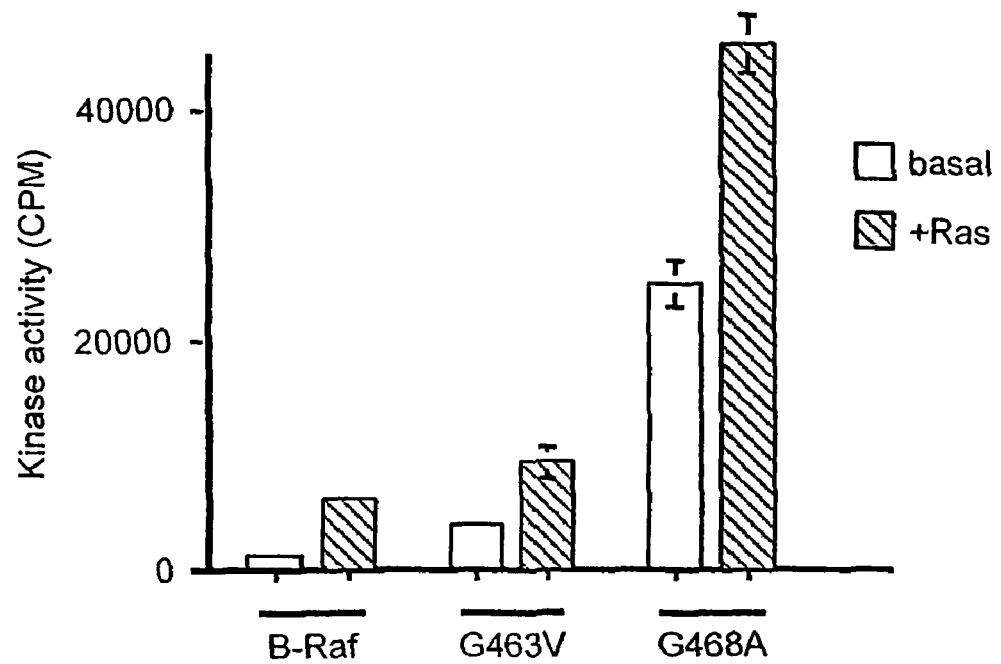
FIG. 1A: B-Raf activity assays. The kinase activity of B-Raf was measured in an immunoprecipation kinase cascade assay, using MBP as the final substrate. The activity is shown as number of counts incorporated into MBP. The assay was performed in triplicate and the average is shown, with error bars to represent deviations from the mean. Both the basal kinase activity (open bars) and the $^{V12}$Ras stimulated kinase activities (hatched bars) are shown.

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) $4^{th}$ Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.). These documents are incorporated herein by reference.

DEFINITIONS

The present application describes B-Raf polypeptide mutants. As used herein, the term "RAF polypeptide" is used to denote a polypeptide of the RAF family. RAF was first identified in a cloned unique acutely transforming replication-defective mouse type C virus, which contained an oncogene v-raf (Rapp, et al. Proc. Nat. Acad. Sci. 80: 4218-4222, 1983). The cellular homologue, c-raf, is present in mammalian DNA. Other homologues have since been discovered in humans and birds, where raf has been shown to be the homologue of the avian oncogene mil. B-Raf is related to RAF, but possesses three additional N-terminal exons. The term "B-Raf" thus encompasses all known human B-Raf homologues and variants, as well as other polypeptides which show sufficient homology to B-Raf to be identified as B-Raf homologues. The term does not include ARAF, CRAF or RAF1. Preferably, B-Raf is identified as a polypeptide having the sequence shown at accession no. NP_004324, nucleic acid accession no. NM_004333.

The term "B-Raf" preferably includes polypeptides which are 85%, 90%, 95%, 96%, 97%, 98% or 99% homologous to NP_004324. Homology comparisons can be conducted by eye, or more usually, with the aid of readily available sequence comparison programs. These commercially available computer programs can calculate percentage (%) homology between two or more sequences.

Percentage homology can be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is -12 for a gap and -4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

A "fragment" of a polypeptide in accordance with the invention is a polypeptide fragment which encompasses the mutant amino acid(s) described in accordance with the invention. The fragment can be any length up to the full length of B-Raf polypeptide; it thus encompasses B-Raf polypeptides which have been truncated by a few amino acids, as well as shorter fragments. Advantageously, fragments are between about 764 and about 5 amino acids in length; preferably about 5 to about 20 amino acids in length; advantageously, between about 10 and about 50 amino acids in length. Fragments according to the invention are useful, inter alia, for immunisation of animals to raise antibodies. Thus, fragments of polypeptides according to the invention advantageously comprise at least one antigenic determinant (epitope) characteristic of mutant B-Raf as described herein. Whether a particular polypeptide fragment retains such antigenic properties can readily be determined by routine methods known in the art. Peptides composed of as few as six amino acid residues ore often found to evoke an immune response.

A "nucleic acid" of the present invention is a nucleic acid which encodes a human B-Raf polypeptide as described above. The term moreover includes those polynucleotides capable of hybridising, under stringent hybridisation conditions, to the naturally occurring nucleic acids identified above, or the complement thereof. "Stringent hybridisation conditions" refers to an overnight incubation at 42° C. in a solution comprising 50% formamide, 5×SSC (750 mM NaCl, 75 mM trisodium citrate), 50 mM sodium phosphate (pH 7.6), 5× Denhardt's solution, 10% dextran sulphate, and 20 pg/ml denatured, sheared salmon sperm DNA, followed by washing the filters in 0.1×SSC at about 65° C.

Although nucleic acids, as referred to herein, are generally natural nucleic acids found in nature, the term can include within its scope modified, artificial nucleic acids having modified backbones or bases, as are known in the art.

A nucleic acid encoding a fragment according to the invention can be the result of nucleic acid amplification of a specific region of a B-raf gene, incorporating a mutation in accordance with the present invention.

An "isolated" polypeptide or nucleic acid, as referred to herein, refers to material removed from its original environment (for example, the natural environment in which it occurs in nature), and thus is altered by the hand of man from its natural state. For example, an isolated polynucleotide could be part of a vector or a composition of matter, or could be contained within a cell, and still be "isolated" because that vector, composition of matter, or particular cell is not the original environment of the polynucleotide. Preferably, the term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polypeptides/nucleic acids of the present invention.

The polypeptides according to the invention comprise one or more mutations. "Mutations" includes amino acid addition, deletion or substitution; advantageously, it refers to amino acid substitutions. Such mutations at the polypeptide level are reflected at the nucleic acid level by addition, deletion or substitution of one or more nucleotides. Generally, such mutations do not alter the reading frame of the nucleic acid. Advantageously, the changes at the nucleic acid level are point mutations, in which a single nucleotide is substituted for another, altering the codon of which it is part to specify a different amino acid.

The mutations in B-Raf identified in the present invention occur naturally, and have not been intentionally induced in cells or tissue by the application of carcinogens or other tumorigenic factors. Thus, the mutations identified herein accurately reflect natural tumorigenesis in human tissues to in vivo. Their detection is thus a far better basis for diagnosis than the detection of mutations identified in rodents after artificial chemical tumour induction.

A "somatic" mutation is a mutation which is not transmitted through the germ line of an organism, and occurs in somatic tissues thereof. Advantageously, a somatic mutation is one which is determined to be somatic though normal/tumour paired sample analysis.

All amino acid and nucleotide numbering used herein starts from amino acid +1 of the B-Raf polypeptide or the first ATG of the nucleotide sequence encoding it.

"Amplification" reactions are nucleic acid reactions which result in specific amplification of target nucleic acids over non-target nucleic acids. The polymerase chain reaction (PCR) is a well known amplification reaction.

An "immunoglobulin" is one of a family of polypeptides which retain the immunoglobulin fold characteristic of immunoglobulin (antibody) molecules, which contains two β sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor). The present invention is preferably applicable to antibodies, which are capable of binding to target antigens with high specificity.

"Antibodies" can be whole antibodies, or antigen-binding fragments thereof. For example, the invention includes fragments such as Fv and Fab, as well as Fab' and F(ab')$_2$, and antibody variants such as scfv, single domain antibodies, Dab antibodies and other antigen-binding antibody-based molecules.

"Cancer" is used herein to refer to neoplastic growth arising from cellular transformation to a neoplastic phenotype. Such cellular transformation often involves genetic mutation; in the context of the present invention, transformation involves genetic mutation by alteration of one or more B-raf genes as described herein.

Methods for Detection of Nucleic Acids

The detection of mutant nucleic acids encoding B-Raf can be employed, in the context of the present invention, to diagnose the presence or predisposition to cellular transformation and cancer. Since mutations in B-raf genes generally occur at the DNA level, the methods of the invention can be based on detection of mutations in genomic DNA, as well as transcripts and proteins themselves. It can be desirable to confirm mutations in genomic DNA by analysis of transcripts and/or polypeptides, in order to ensure that the detected mutation is indeed expressed in the subject.

Mutations in genomic nucleic acid are advantageously detected by techniques based on mobility shift in amplified nucleic acid fragments. For instance, Chen et al., Anal Biochem Jul. 15, 1996;239(1):61-9, describe the detection of single-base mutations by a competitive mobility shift assay. Moreover, assays based on the technique of Marcelino et al., BioTechniques 26(6): 1134-1148 (June 1999) are available commercially.

In a preferred example, capillary heteroduplex analysis may be used to detect the presence of mutations based on mobility shift of duplex nucleic acids in capillary systems as a result of the presence of mismatches.

Generation of nucleic acids for analysis from samples generally requires nucleic acid amplification. Many amplification methods rely on an enzymatic chain reaction (such as a polymerase chain reaction, a ligase chain reaction, or a self-sustained sequence replication) or from the replication of all or part of the vector into which it has been cloned. Preferably, the amplification according to the invention is an exponential amplification, as exhibited by for example the polymerase chain reaction.

Many target and signal amplification methods have been described in the literature, for example, general reviews of these methods in Landegren, U., et al., Science 242:229-237 (1988) and Lewis, R., Genetic Engineering News 10:1, 54-55 (1990). These amplification methods can be used in the methods of our invention, and include polymerase chain reaction (PCR), PCR in situ, ligase amplification reaction (LAR), ligase hybridisation, Qbeta bacteriophage replicase, transcription-based amplification system (TAS), genomic amplification with transcript sequencing (GAWTS), nucleic acid sequence-based amplification (NASBA) and in situ. hybridisation. Primers suitable for use in various amplification techniques can be prepared according to methods known in the art.

Polymerase Chain Reaction (PCR)

PCR is a nucleic acid amplification method described inter alia in U.S. Pat. Nos. 4,683,195 and 4,683,202. PCR consists of repeated cycles of DNA polymerase generated primer extension reactions. The target DNA is heat denatured and two oligonucleotides, which bracket the target sequence on opposite strands of the DNA to be amplified, are hybridised. These oligonucleotides become primers for use with DNA polymerase. The DNA is copied by primer extension to make a second copy of both strands. By repeating the cycle of heat denaturation, primer hybridisation and extension, the target DNA can be amplified a million fold or more in about two to four hours. PCR is a molecular biology tool, which must be used in conjunction with a detection technique to determine the results of amplification. An advantage of PCR is that it increases sensitivity by amplifying the amount of target DNA by 1 million to 1 billion fold in approximately 4 hours. PCR can be used to amplify any known nucleic acid in a diagnostic context (Mok et al., (1994), Gynaecologic Oncology, 52: 247-252).

Self-Sustained Sequence Replication (3SR)

Self-sustained sequence replication (3SR) is a variation of TAS, which involves the isothermal amplification of a nucleic acid template via sequential rounds of reverse transcriptase (RT), polymerase and nuclease activities that are mediated by an enzyme cocktail and appropriate oligonucleotide primers (Guatelli et al. (1990) Proc. Natl. Acad. Sci. USA 87:1874). Enzymatic degradation of the RNA of the RNA/DNA heteroduplex is used instead of heat denaturation. RNase H and all other enzymes are added to the reaction and all steps occur at the same temperature and without further reagent additions. Following this process, amplifications of $10^6$ to $10^9$ have been achieved in one hour at 42° C.

Ligation Amplification (LAR/LAS)

Ligation amplification reaction or ligation amplification system uses DNA ligase and four oligonucleotides, two per target strand. This technique is described by Wu, D. Y. and Wallace, R. B. (1989) Genomics 4:560. The oligonucleotides hybridise to adjacent sequences on the target DNA and are joined by the ligase. The reaction is heat denatured and the cycle repeated.

Qβ Replicase

In this technique, RNA replicase for the bacteriophage Qβ, which replicates single-stranded RNA, is used to amplify the target DNA, as described by Lizardi et al. (1988) Bio/Technology 6:1197. First, the target DNA is hybridised to a primer including a T7 promoter and a Qβ 5' sequence region. Using this primer, reverse transcriptase generates a cDNA connecting the primer to its 5' end in the process. These two steps are similar to the TAS protocol. The resulting heteroduplex is heat denatured. Next, a second primer containing a Qβ 3' sequence region is used to initiate a second round of cDNA synthesis. This results in a double stranded DNA containing both 5' and 3' ends of the Qβ bacteriophage as well as an active T7 RNA polymerase binding site. T7 RNA polymerase then transcribes the double-stranded DNA into new RNA, which minics the Qβ. After extensive washing to remove any unhybridised probe, the new RNA is eluted from the target and replicated by Qβ replicase. The latter reaction creates $10^7$ fold amplification in approximately 20 minutes.

Alternative amplification technology can be exploited in the present invention. For example, rolling circle amplification (Lizardi et al., (1998) Nat Genet 19:225) is an amplification technology available commercially (RCAT™) which is driven by DNA polymerase and can replicate circular oligonucleotide probes with either linear or geometric kinetics under isothermal conditions.

In the presence of two suitably designed primers, a geometric amplification occurs via DNA strand displacement and hyperbranching to generate 1012 or more copies of each circle in 1 hour.

If a single primer is used, RCAT generates in a few minutes a linear chain of thousands of tandemly linked DNA copies of a target covalently linked to that target.

A further technique, strand displacement amplification (SDA; Walker et al., (1992) PNAS (USA) 80:392) begins with a specifically defined sequence unique to a specific target. But unlike other techniques which rely on thermal cycling, SDA is an isothermal process that utilises a series of primers, DNA polymerase and a restriction enzyme to exponentially amplify the unique nucleic acid sequence.

SDA comprises both a target generation phase and an exponential amplification phase.

In target generation, double-stranded DNA is heat denatured creating two single-stranded copies. A series of specially manufactured primers combine with DNA polymerase (amplification primers for copying the base sequence and bumper primers for displacing the newly created; strands) to form altered targets capable of exponential amplification.

The exponential amplification process begins with altered targets (single-stranded partial DNA strands with restricted enzyme recognition sites) from the target generation phase.

An amplification primer is bound to each strand at its complementary DNA sequence. DNA polymerase then uses the primer to identify a location to extend the primer from its 3' end, using the altered target as a template for adding individual nucleotides. The extended primer thus forms a double-stranded DNA segment containing a complete restriction enzyme recognition site at each end.

A restriction enzyme is then bound to the double stranded DNA segment at its recognition site. The restriction enzyme dissociates from the recognition site after having cleaved only one strand of the double-sided segment, forming a nick. DNA polymerase recognises the nick and extends the strand from the site, displacing the previously created strand. The recognition site is thus repeatedly nicked and restored by the restriction enzyme and DNA polymerase with continuous displacement of DNA strands containing the target segment.

Each displaced strand is then available to anneal with amplification primers as above. The process continues with repeated nicking, extension and displacement of new DNA strands, resulting in exponential amplification of the original DNA target.

Once the nucleic acid has been amplified, a number of techniques are available for detection of single base pair mutations. One such technique is Single Stranded Conformational Polymorphism (SSCP). SCCP detection is based on the aberrant migration of single stranded mutated DNA compared to reference DNA during electrophoresis. Mutation produces conformational change in single stranded DNA, resulting in mobility shift. Fluorescent SCCP uses fluorescent-labelled primers to aid detection. Reference and mutant DNA are thus amplified using fluorescent labelled primers. The amplified DNA is denatured and snap-cooled to produce single stranded DNA molecules, which are examined by non-denaturing gel electrophoresis.

Chemical mismatch cleavage (CMC) is based on the recognition and cleavage of DNA mismatched base pairs by a combination of hydroxylamine, osmium tetroxide and piperidine. Thus, both reference DNA and mutant DNA are amplified with fluorescent labelled primers. The amplicons are hybridised and then subjected to cleavage using Osmium tetroxide, which binds to an mismatched T base, or Hydroxylamine, which binds to mismatched C base, followed by Piperidine which cleaves at the site of a modified base. Cleaved fragments are then detected by electrophoresis.

Techniques based on restriction fragment polymorphisms (RFLPs) can also be used. Although many single nucleotide polymorphisms (SNPs) do not permit conventional RFLP analysis, primer-induced restriction analysis PCR (PIRA-PCR) can be used to introduce restriction sites using PCR primers in a SNP-dependent manner. Primers for PIRA-PCR which introduce suitable restriction sites can be designed by computational analysis, for example as described in Xiaiyi et al., (2001) Bioinformatics 17:838-839.

In an alternative embodiment, the present invention provides for the detection of gene expression at the RNA level. Typical assay formats utilising ribonucleic acid hybridisation include nuclear run-on assays, RT-PCR and RNase protection assays (Melton et al., Nuc. Acids Res. 12:7035. Methods for detection which can be employed include radioactive labels, enzyme labels, chemiluminescent labels, fluorescent labels and other suitable labels.

RT-PCR is used to amplify RNA targets. In this process, the reverse transcriptase enzyme is used to convert RNA to complementary DNA (cDNA), which can then be amplified using PCR. This method has proven useful for the detection of RNA viruses. Its application is otherwise as for PCR, described above.

Methods for Detection of Polypeptides

The invention provides a method wherein a protein encoded a mutant B-raf gene is detected. Proteins can be detected by protein gel assay, antibody binding assay, or other detection methods known in the art.

For example, therefore, mutant B-Raf polypeptides can be detected by differential mobility on protein gels, or by other size analysis techniques such as mass spectrometry, in which the presence of mutant amino acids can be determined according to molecular weight. Peptides derived from mutant B-Raf polypeptides, in particular, as susceptible to differentiation by size analysis.

Advantageously, the detection means is sequence-specific, such that a particular point mutation can accurately be identified in the mutant B-Raf polypeptide. For example, polypeptide or RNA molecules can be developed which specifically recognise mutant B-Raf polypeptides in vivo or in vitro.

For example, RNA aptamers can be produced by SELEX. SELEX is a method for the in vitro evolution of nucleic acid molecules with highly specific binding to target molecules. It is described, for example, in U.S. Pat. Nos. 5,654,151, 5,503, 978, 5,567,588 and 5,270,163, as well as PCT publication WO 96/38579, each of which is specifically incorporated herein by reference.

The SELEX method involves selection of nucleic acid aptamers, single-stranded nucleic acids capable of binding to a desired target, from a library of oligonucleotides. Starting from a library of nucleic acids, preferably comprising a segment of randomised sequence, the SELEX method includes steps of contacting the library with the target under conditions favourable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched library of nucleic acids, then reiterating the steps of binding, partitioning, dissociating and amplifying through as many cycles as desired to yield highly specific, high affinity nucleic acid ligands to the target molecule.

SELEX is based on the principle that within a nucleic acid library containing a large number of possible sequences and structures there is a wide range of binding affinities for a given target. A nucleic acid library comprising, for example a 20 nucleotide randomised segment can have $4^{20}$ structural possibilities. Those which have the higher affinity constants for the target are considered to be most likely to bind. The process of partitioning, dissociation and amplification generates a second nucleic acid library, enriched for the higher binding affinity candidates. Additional rounds of selection progressively favour the best ligands until the resulting library is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The iterative selection/amplification method is sensitive enough to allow isolation of a single sequence variant in a library containing at least $10^{14}$ sequences. The method could, in principle, be used to sample as many as about $10^{18}$ different nucleic acid species. The nucleic acids of the library preferably include a randomised sequence portion as well as conserved sequences necessary for efficient amplification. Nucleic acid sequence variants can be produced in a number of ways including synthesis of randomised nucleic acid sequences and size selection from randomly cleaved cellular nucleic acids. The variable sequence portion can contain fully or partially random sequence; it can also contain subportions of conserved sequence incorporated with randomised sequence. Sequence variation in test nucleic acids can be introduced or increased by mutagenesis before or during the selection/amplification iterations and by specific modification of cloned aptamers.

Antibodies P B-Raf polypeptides or peptides derived therefrom can be used to generate antibodies for use in the present invention. The B-Raf peptides used preferably comprise an epitope which is specific for a mutant B-Raf polypeptide in accordance with the invention. Polypeptide fragments which function as epitopes can be produced by any conventional means (see, for example, U.S. Pat. No. 4,631,211) In the present invention, antigenic epitopes preferably contain a sequence of at least 4, at least 5, at least 6, at least 7, more preferably at least 8, at least 9, at least 10, at least 1, at least 12, at least 13, at least 14, at least 15, at least 20, at least 25, at least 30, at least 40, at least 50. and, most preferably, between about 15 to about 30 amino acids. Preferred polypeptides comprising immunogenic or antigenic epitopes are at least 25, 30, 35, 40, 45, 50, 55, 60, 65, 70, 75, 80, 85, 90, 95 or 100 amino acid residues in length.

Antibodies can be generated using antigenic epitopes of B-Raf polypeptides according to the invention by immunising animals, such as rabbits or mice, with either free or carrier-coupled peptides, for instance, by intraperitoneal and/or intradermal injection of emulsions containing about 100 μg of peptide or-carrier protein and Freund's adjuvant or any other adjuvant known for stimulating an immune response. Several booster injections can be needed, for instance, at intervals of about two weeks, to provide a useful titre of anti-peptide antibody which can be detected, for example, by ELISA assay using free peptide adsorbed to a solid surface. The titre of anti-peptide antibodies in serum from an immunised animal can be increased by selection of anti-peptide antibodies, for instance, by adsorption to the peptide on a solid support and elution of the selected antibodies according to methods well known in the art.

The B-Raf polypeptides of the present invention, and immunogenic and/or antigenic epitope fragments thereof can be fused to other polypeptide sequences. For example, the polypeptides of the present invention can be fused with immunoglobulin domains. Chimeric proteins consisting of the first two domains of the human CD4-polypeptide and various domains of the constant regions of the heavy or light chains of mammalian immunoglobulins have been shown to possess advantageous properties in vivo (see, for example, EP 0394827; Traunecker et al., (1988) Nature, 331: 84-86). Enhanced delivery of an antigen across the epithelial barrier to the immune system has been demonstrated for antigens (such as insulin) conjugated to an FcRn binding partner such as IgG or Fc fragments (see, for example, WO 96/22024 and WO 99/04813).

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86: 821-824 (1989), for instance, hexa-histidine provides for convenient purification of the fusion protein. Another peptide tag useful for purification, the "HA" tag, corresponds to an epitope derived from the influenza hemagglutinin protein (Wilson et al., (1984) Cell 37: 767. Thus, any of these above fusions can be engineered using the nucleic acids or the polypeptides of the present invention.

In a preferred embodiment, the, invention provides antibodies which specifically recognise B.-Raf mutants as described herein.

Antibodies as described herein are especially indicated for diagnostic applications. Accordingly, they can be altered antibodies comprising an effector protein such as a label. Especially preferred are labels which allow the imaging of the distribution of the antibody in vivo. Such labels can be radioactive labels or radioopaque labels, such as metal particles, which are readily visualisable within the body of a patient. Moreover, they can be fluorescent labels or other labels which are visualisable on tissue Recombinant DNA technology can be used to improve the antibodies of the invention. Thus, chimeric antibodies can be constructed in order to decrease the immunogenicity thereof in diagnostic or therapeutic applications. Moreover, immunogenicity can be minimised by humanising the antibodies by CDR grafting [see European Patent Application 0 239 400 (Winter)] and, optionally, framework modification [EP 0 239 400; Riechrnann, L. et al., Nature, 332, 323-327, 1988; Verhoeyen M. et al., Science, 239, 1534-1536, 1988; Kettleborough, C. A. et al., Protein Engng., 4, 773-783, 1991; Maeda, H. et al., Human Antibodies and Hybridoma, 2, 124-134, 1991; Gorman S. D. et al., Proc. Nati. Acad. Sci. USA, 88, 4181-4185, 1991; Tempest P. R. et al., Bio/Technology, 9, 266-271, 1991; Co, M. S. et al., Proc. Natl. Acad. Sci. USA, 88, 2869-2873, 1991; Carter, P. et al., Proc. Natl. Acad. Sci. USA, 89,-4285-4289, 1992; Co, M. S. et al., J. Immunol., 148, 1149-1154, 1992; and, Sato, K. et al., Cancer Res., 53, 851-856, 1993].

Antibodies as described herein can be produced in cell culture. Recombinant DNA technology can be used to produce the antibodies according to established procedure, in bacterial or preferably mammalian cell culture. The selected cell culture system optionally secretes the antibody product, although antibody products can be isolated from non-secreting cells.

Therefore, the present, invention includes a process for the production of an antibody according to the invention comprising culturing a host, e.g. *E. coli*, an insect cell or a mammalian cell, which has been transformed with a hybrid vector comprising an expression cassette comprising a promoter operably linked to a first DNA sequence encoding a signal peptide linked in the proper reading frame to a second DNA sequence encoding said antibody protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2× YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation, are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetrametlyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; US 4,376,110; Harlow and Lane, Antibodies: a Laboratory Manual, (1988) Cold Spring Harbor, incorporated herein by reference. Techniques for the preparation of recombinant antibody molecules is described in the above references and also in, for example, EP 0623679; EP 0368684 and EP 0436597, which are incorporated herein by reference.

The cell culture supernatants are screened for the desired antibodies, preferentially by an enzyme immunoassay, e.g. a sandwich assay or a dot-assay, or a radioimmunoassay.

For isolation of the antibodies, the immunoglobulins in the culture supernatants or in the ascitic fluid can be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with the target antigen, or with Protein-A.

The invention further concerns hybridoma cells secreting the monoclonal antibodies of the invention. The preferred hybridoma cells of the invention are genetically stable, secrete monoclonal antibodies of the invention of the desired specificity and can be activated from deep-frozen cultures by thawing and recloning.

The invention, in a preferred embodiment, relates to the production of anti mutant B-Raf antibodies. Thus, the invention also concerns a process for the preparation of a hybridoma cell line secreting monoclonal antibodies according to the invention, characterised in that a suitable mammal, for example a Balb/c mouse, is immunised with a one or more PDGF polypeptides or antigenic fragments thereof, or an antigenic carrier containing a mutant B-Raf polypeptide; antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with mutant B-Raf are fused with cells of the myeloma cell line PAI or the myeloma cell line Sp2/0-Ag14, the obtained hybrid cells are screened for secretion of the desired antibodies, and positive hybridoma cells are cloned.

Preferred is a process for the preparation of a hybridoma cell line, characterised in that Balb/c mice are immunised by injecting subcutaneously and/or intraperitoneally between 1 and 100 µg mutant B-Raf and a suitable adjuvant, such as Freund's adjuvant, several times, e.g. four to six times, over several months, e.g. between two and four months, and spleen cells from the immunised mice are taken two to four days after the last injection and fused with cells of the myeloma cell line PAI in the presence of a fusion promoter, preferably polyethylene glycol. Preferably the myeloma cells are fused with a three-to twentyfold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

The invention also concerns recombinant nucleic acids comprising an insert coding for a heavy chain variable domain and/or for a light chain variable domain of antibodies directed to mutant B-Raf as described hereinbefore. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed to mutant B-Raf can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences can be useful due to their different restriction sites and/or frequency of particular codons which are preferred by the specific host, particularly *E. coli*, to obtain an optimal expression of the heavy chain murine variable domain and/or a light chain murine variable domain.

In this context, the term mutant is intended to include a DNA mutant obtained by in vitro mutagenesis of the authentic DNA according to methods known in the art.

For the assembly of complete tetrameric imnmunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

The invention therefore also concerns recombinant nucleic acids comprising an insert coding for a heavy chain murine variable domain of an anti mutant B-Raf antibody fused to a human constant domain γ, for example γ1, γ2, γ3 or γ4, preferably γ1 or γ4. Likewise the invention concerns recombinant DNAs comprising an insert coding for a light chain murine variable domain of an anti mutant B-Raf antibody directed to mutant B-Raf fused to a human constant domain κ or λ, preferably κ.

In another embodiment the invention pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule.

Antibodies and antibody fragments according to the invention are useful in diagnosis. Accordingly, the invention provides a composition for diagnosis comprising an antibody according to the invention.

In the case of a diagnostic composition, the antibody is preferably provided together with means for detecting the antibody, which can be enzymatic, fluorescent, radioisotopic or other means. The antibody and the detection means can be provided for simultaneous, simultaneous separate or sequential use, in a diagnostic kit intended for diagnosis.

The antibodies of the invention can be assayed for immunospecific binding by any method known in the art. The immunoassays which can be used include but are not limited to competitive and non-competitive assay systems using techniques such as western blots, radioimmunoassays, ELISA, sandwich immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Such assays are routine in the art (see, for example, Ausubel et al, eds, 1994, Current Protocols in Molecular Biology, Vol. 1, John Wiley &s Sons, Inc., New York, which is incorporated by reference herein in its entirety). Exemplary immunoassays are described briefly below.

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2,1% Trasylol) supplemented with protein phosphatase and/or protease inhibitors (e. g., EDTA, PMSF, aprotinin, sodium vanadate), adding the antibody of interest to the cell lysate, incubating for a period of time (e.g., 1-4 hours) at 4 ° C., adding protein A and/or protein G sepharose beads to the cell lysate, incubating for about an hour or more at 4 ° C., washing the beads in lysis buffer and resuspending the beads in SDS/sample buffer. The ability of the antibody of interest to immunoprecipitate a particular antigen can be assessed by, e.g., western blot analysis.

Western blot analysis generally comprises preparing protein samples, electrophoresis of he protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), exposing the membrane to a primary antibody (the antibody of interest) diluted in blocking buffer, washing the membrane in washing buffer, exposing the membrane to a secondary antibody (which recognises the primary antibody, e.g., an antihuman antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen.

ELISAs comprise preparing antigen, coating the well of a 96 well microtitre plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognises the antibody of interest) conjugated to a detectable compound can be added to the well. Further, instead of coating the well with the antigen, the antibody can be coated to the well. In this case, a second antibody conjugated to a detectable compound can be added following the addition of the antigen of interest to the coated well.

The binding affinity of an antibody to an antigen and the off-rate of an antibody-antigen interaction can be determined by competitive binding assays. One example of a competitive binding assay is a radioimmunoassay comprising the incubation of labelled antigen (e.g., $^{3}H$ or $^{125}I$) with the antibody of interest in the presence of increasing amounts of unlabeled antigen, and the detection of the antibody bound to the labelled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labelled compound (e.g., $^{3}H$ or $^{125}I$) in the presence of increasing amounts of an unlabeled second antibody.

Preparation of mutant B-Raf Polypeptides

Mutant B-Raf polypeptides in accordance with the present invention can be produced by any desired technique, including chemical synthesis, isolation from biological samples and expression of a nucleic acid encoding such a polypeptide. Nucleic acids, in their turn, can be synthesised or isolated from biological sources of mutant B-Raf.

The invention thus relates to vectors encoding a polypeptide according to the invention, or a fragment thereof. The vector can be, for example, a phage, plasmid, viral, or retroviral vector.

Nucleic acids according to the invention can be part of a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The nucleic acid insert is operatively linked to an appropriate promoter, such as the phage lambda PL promoter, the *E. coli* lac, trp, phoA and tac promoters, the SV40 early and late promoters and promoters of retroviral LTRs. Other suitable promoters are known to those skilled in the art. The expression constructs further contain sites for transcription initiation, termination, and, in the transcribed region, a ribosome binding site for translation. The coding portion of the transcripts expressed by the constructs preferably includes a translation initiating codon at the beginning, and a termination codon (UAA, UGA or UAG) appropriately positioned at the end of the polypeptide to be translated.

As indicated, the expression vectors preferably include at least one selectable marker. Such markers include dihydrofolate reductase, G418 or neomycin resistance for eukaryotic cell culture and tetracycline, kanamycin or ampicillin resistance aenes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris*); insect cells such as *Drosophila* S2 and *Spodoptera* Sf9 cells; animal cells such as CHO, COS, 293, and Bowes melanoma cells; and plant cells.

Appropriate culture media and conditions for the above-described host cells are known in the art and available commercially.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK2233, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PA0815 (all available from Invitrogen, Carlsbad, Calif.).

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Sambrook et al., referred to above.

A polypeptide according to the invention can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides according to the present invention can also be recovered from biological sources, including bodily fluids, tissues and cells, especially cells derived from tumour tissue or suspected tumour tissues from a subject.

In addition, polypeptides according to the invention can be chemically synthesised using techniques known in the art (for example, see Creighton, 1983, Proteins: Structures and Molecular Principles, W. H. Freeman & Co., N. Y., and Hunkapiller et al., Nature, 310: 105-111 (1984)). For example, a polypeptide corresponding to a fragment of a mutant B-Raf polypeptide can be synthesised by use of a peptide synthesiser.

B-Raf Mutations

Mutations in B-Raf have been identified in human tumour cells. Table 1 describes the location of these mutations and the tumours in which they were identified. The mutations are in the kinase domain of B-Raf. Most of the mutations can be confirmed as somatic, indicating that a paired normal/tumour sample was tested and the mutation found only in the tumour sample.

TABLE 1

| Gene | cDNA accession No. | Protein accession No. | Nucleic acid mutation | Protein mutation | Tumour | Tumour type | Somatic |
|---|---|---|---|---|---|---|---|
| B-Raf | NM_004333 | NP_004324 | T1796A | V599E | A101D | melanoma | N/a |
| B-Raf | NM_004333 | NP_004324 | T1796A | V599E | A2058 | melanoma | N/a |
| B-Raf | NM_004333 | NP_004324 | T1796A | V599E | A375 | melanoma | N/a |
| B-Raf | NM_004333 | NP_004324 | T1796A | V599E | A673 | Sarcoma (Ewings) | N/a |
| B-Raf | NM_004333 | NP_004324 | T1796A | V599E | C32 | melanoma | N/a |
| B-Raf | NM_004333 | NP_004324 | T1796A | V599E | COLO-205 | colorectal | N/a |
| B-Raf | NM_004333 | NP_004324 | T1796A | V599E | COLO-679 | melanoma | N/a |
| B-Raf | NM_004333 | NP_004324 | T1796A | V599E | COLO-741 | colorectal | N/a |
| B-Raf | NM_004333 | NP_004324 | T1796A | V599E | COLO-800 | melanoma | N/a |
| B-Raf | NM_004333 | NP_004324 | T1796A | V599E | Colo829 | Malignant melanoma | Yes |
| B-Raf | NM_004333 | NP_004324 | T1796A | V599E | Colo-829 | Melanoma cell line pair | Yes |
| B-Raf | NM_004333 | NP_004324 | T1796A p-loop | V599E | Colon DBTRG-05MG | glioma | N/a |
| B-Raf | NM_004333 | NP_004324 | T1796A | V599E | DU-4475 | Breast cancer | N/a |
| B-Raf | NM_004333 | NP_004324 | T1796A | V599E | DU-4475 | Breast | N/a |
| B-Raf | NM_004333 | NP_004324 | T1796A | V599E | Duke Mel 103 | melanoma | Yes |
| B-Raf | NM_004333 | NP_004324 | T1796A | V599E | Duke Mel 104 | melanoma | Yes |
| B-Raf | NM_004333 | NP_004324 | G1394C | G465A | Duke Mel 105 | melanoma | Yes |
| B-Raf | NM_004333 | NP_004324 | T1796A | V599E | Duke Mel 108 | melanoma | Yes |
| B-Raf | NM_004333 | NP_004324 | T1796A | V599E | Duke Mel 110 | melanoma | Yes |
| B-Raf | NM_004333 | NP_004324 | T1796A | V599E | Duke Mel 111 | melanoma | Yes |
| B-Raf | NM_004333 | NP_004324 | T1796A | V599E | Duke Mel 113 | melanoma | Yes |
| B-Raf | NM_004333 | NP_004324 | T1796A | V599E | Duke Mel 115 | melanoma | Yes |
| B-Raf | NM_004333 | NP_004324 | T1796A | V599E | Duke Mel 114 | melanoma | Yes |
| B-Raf | NM_004333 | NP_004324 | T1796A | V599E | G-361 | melanoma | N/a |
| B-Raf | NM_004333 | NP_004324 | T1796A | V599E | GCT | Sarcoma (GCT/histiocytoma) | N/a |
| B-Raf | NM_004333 | NP_004324 | T1796A | V599E | HT-144 | melanoma | N/a |
| B-Raf | NM_004333 | NP_004324 | T1796A | V599E | HT29 | Colorectal cancer | N/a |
| B-Raf | NM_004333 | NP_004324 | T1796A | V599E | HT29 | colorectal | N/a |
| B-Raf | NM_004333 | NP_004324 | G1388A | G463E | Hx62-26 | Ovary/bladder? | N/a |
| B-Raf | NM_004333 | NP_004324 | T1796A | V599E | HxLL | melanoma | N/a |
| B-Raf | NM_004333 | NP_004324 | T1796A | V599E | KG-1-C | glioma | N/a |
| B-Raf | NM_004333 | NP_004324 | T1796A p-loop | V599E | LS-411N Lung | colorectal | N/a |
| B-Raf | NM_004333 | NP_004324 | T1796A | V599E | Malme-3M | Malignant melanoma | N/a |
| B-Raf | NM_004333 | NP_004324 | T1796A | V599E | Malme-3M | melanoma | N/a |
| B-Raf | NM_004333 | NP_004324 | G1388T | G463V | MDA-MB-231 | Breast | N/a |
| B-Raf | NM_004333 | NP_004324 | T1796A | V599E | MDA-MB-435 | Breast cancer | N/a |
| B-Raf | NM_004333 | NP_004324 | T1796A | V599E | MDA-MB-435 | Breast | N/a |

TABLE 1-continued

| Gene | cDNA accession No. | Protein accession No. | Nucleic acid mutation | Protein mutation | Tumour | Tumour type | Somatic |
|---|---|---|---|---|---|---|---|
| B-Raf | NM_004333 | NP_004324 | G1403C | G468A | NCI-H1395 | NSCLC | N/a |
| B-Raf | NM_004333 | NP_004324 | G1394T | G465V | NCI-H1666 | NSCLC | N/a |
| B-Raf | NM_004333 | NP_004324 | G1403C | G468A | NCI-H1755 | NSCLC | N/a |
| B-Raf | NM_004333 | NP_004324 | C1786G | L596V | NCI-H2087 | NSCLC | Yes |
| B-Raf | NM_004333 | NP_004324 | C1786G | L596V | NCI-H2087 | NSCLC | N/a |
| B-Raf | NM_004333 | NP_004324 | G1783C | G595R | NCI-H508 | colorectal | N/a |
| B-Raf | NM_004333 | NP_004324 | T1796A | V599E | NMC-G1 | glioma | N/a |
| B-Raf | NM_004333 | NP_004324 | T1795A | V599E | Ov-90-93 | Ovarian cancer | Yes |
| B-Raf | NM_004333 | NP_004324 | T1796A | V599E | PT-18-92-T | Ovarian cancer | Yes |
| B-Raf | NM_004333 | NP_004324 | G1753A | E585K | PT-52-91-T | Ovarian cancer | Yes |
| B-Raf | NM_004333 | NP_004324 | T1787G | L596R | PT-66-91-T | Ovarian cancer | Yes |
| B-Raf | NM_004333 | NP_004324 | T1796A | V599E | PT-93-13956-T | Colon cancer, hk | Yes |
| B-Raf | NM_004333 | NP_004324 | T1796A | V599E | PT-93-7014T | Colon cancer, HK | Yes |
| B-Raf | NM_004333 | NP_004324 | T1796A | V599E | PT-93-7014-T | Colon cancer, HK | Yes |
| B-Raf | NM_004333 | NP_004324 | T1782G | F594L | PT-97-51-T | Colon adenocarcinoma, Duke | Yes |
| B-Raf | NM_004333 | NP_004324 | C1786G | L596V | PT-97-51-T | Colon adenocarcinoma, Duke | Yes |
| B-Raf | NM_004333 | NP_004324 | T1796A | V599E | PT-97-93-T | Ovarian cancer | Yes |
| B-Raf | NM_004333 | NP_004324 | T1796A | V599E | RPMI-7951 | melanoma | N/a |
| B-Raf | NM_004333 | NP_004324 | T1796A | V599E | RUCH2-DH | rhabdomyosarcoma | N/a |
| B-Raf | NM_004333 | NP_004324 | T1796A | V599E | Sarcoma 24 | Histiocytoma | Yes |
| B-Raf | NM_004333 | NP_004324 | T1796A | V599E | SH-4 | melanoma | N/a |
| B-Raf | NM_004333 | NP_004324 | T1796A | V599E | S86-5261 | melanoma | N/a |
| B-Raf | NM_004333 | NP_004324 | T1796A | V599E | S93-11360 | melanoma | N/a |
| B-Raf | NM_004333 | NP_004324 | T1796A | V599E | S94-6209 | melanoma | N/a |
| B-Raf | NM_004333 | NP_004324 | T1796A | V599E | S95-10334 | melanoma | N/a |
| B-Raf | NM_004333 | NP_004324 | T1796A | V599E | S99-11631 | melanoma | N/a |
| B-Raf | NM_004333 | NP_004324 | T1796A | V599E | SK-HEP-1 | hepatocellular | N/a |
| B-Raf | NM_004333 | NP_004324 | T1796A | V599E | SK-MEL-24 | melanoma | N/a |
| B-Raf | NM_004333 | NP_004324 | T1796A | V599E | SK-MEL-28 | melanoma | N/a |
| B-Raf | NM_004333 | NP_004324 | T1796A | V599E | SK-MEL-3 | melanoma | N/a |
| B-Raf | NM_004333 | NP_004324 | T1796A | V599E | SW1417 | colorectal | N/a |
| B-Raf | NM_004333 | NP_004324 | T1796A | V599E | SW872 | Sarcoma (liposarcoma) | N/a |
| B-Raf | NM_004333 | NP_004324 | T1796A | V599E | TE-159-T | rhabdomyosarcoma | N/a |
| B-Raf | NM_004333 | NP_004324 | T1796A | V599E | AM-38 | glioma | N/a |
| B-Raf | NM_004333 | NP_004324 | TG1796-97AT | V599E | WM-266-4/WM-115 | melanoma | N/a |
| B-Raf | NM_004333 | NP_004324 | G2041A | R681Q | HEC-1-A | Uterus | N/a |
| B-Raf | NM_004333 | NP_004324 | T974C | I325T | ZR-75-30 | Breast | N/a |

Compound Assays

According to the present invention, mutant B-Raf is used as a target to identify compounds, for example lead compounds for pharmaceuticals, which are capable of modulating the proliferative activity of mutant B-Raf. Accordingly, the invention relates to an assay and provides a method for identifying a compound or compounds capable, directly or indirectly, of modulating the activity mutant B-Raf, comprising the steps of:

(a) incubating mutant B-Raf with the compound or compounds to be assessed; and
(b) identifying those compounds which influence the activity of mutant B-Raf.

Mutant B-Raf is as defined in the context of the present invention.

According to a first embodiment of this aspect invention, the assay is configured to detect polypeptides which bind directly to mutant B-Raf.

The invention therefore provides a method for identifying a modulator cell proliferation, comprising the steps of:

(a) incubating mutant B-Raf with the compound or compounds to be assessed; and
(b) identifying those compounds which bind to mutant B-Raf.

Preferably, the method further comprises the step of:

(c) assessing the compounds which bind to mutant B-Raf for the ability to modulate cell proliferation in a cell-based assay.

Binding to mutant B-Raf may be assessed by any technique known to those skilled in the art. Examples of suitable assays include the two hybrid assay system, which measures interactions in vivo, affinity chromatography assays, for example involving binding to polypeptides immobilised on a column, fluorescence assays in which binding of the compound(s) and mutant B-Raf is associated with a change in fluorescence of one or both partners in a binding pair, and the like. Preferred are assays performed in vivo in cells, such as the two-hybrid assay.

In a preferred aspect of this embodiment, the invention provides a method for identifying a lead compound for a pharmaceutical useful in the treatment of disease involving or using cell proliferation, comprising incubating a compound or compounds to be tested with mutant B-Raf, under conditions in which, but for the presence of the compound or compounds to be tested, B-Raf associates with RAS with a reference affinity;

determining the binding affinity of mutant B-Raf for RAS in the presence of the compound or compounds to be tested; and selecting those compounds which modulate the binding affinity of mutant B-Raf for RAS with respect to the reference binding affinity.

Preferably, therefore, the assay according to the invention is calibrated in absence of the compound or compounds to be tested, or in the presence of a reference compound whose activity in binding to mutant B-Raf is known or is otherwise desirable as a reference value. For example, in a two-hybrid system, a reference value may be obtained in the absence of any compound. Addition of a compound or compounds which increase the binding affinity of mutant B-Raf for a target increases the readout from the assay above the reference level, whilst addition of a compound or compounds which decrease this affinity results in a decrease of the assay readout below the reference level.

In a second embodiment, the invention may be configured to detect functional interactions between a compound or compounds and mutant B-Raf. Such interactions will occur either at the level of the regulation of mutant B-Raf, such that this kinase is itself activated or inactivated, for example by RAS, in response to the compound or compounds to be tested, or at the level of the modulation of the biological effect of mutant B-Raf on downstream targets such as MEK. As used herein, "activation" and "inactivation" include modulation of the activity, enzymatic or otherwise, of a compound, as well as the modulation of the rate of production thereof, for example by the activation or repression of expression of a polypeptide in a cell. The terms include direct action on gene transcription in order to modulate the expression of a gene product.

Assays which detect modulation of the functional interaction between mutant B-Raf and its upstream or downstream partners in a signalling pathway are preferably cell-based assays. For example, they may be based on an assessment of the degree of phosphorylation of MAPK, which is indicative of the degree of MEK activation, resulting from activation of mutant B-Raf.

In preferred embodiments, a nucleic acid encoding mutant B-Raf is ligated into a vector, and introduced into suitable host cells to produce transformed cell lines that express mutant B-Raf. The resulting cell lines can then be produced for reproducible qualitative and/or quantitative analysis of the effect(s) of potential compounds affecting mutant B-Raf function. Thus mutant B-Raf expressing cells may be employed for the identification of compounds, particularly low molecular weight compounds, which modulate the function of mutant B-Raf Thus host cells expressing mutant B-Raf are useful for drug screening and it is a further object of the present invention to provide a method for identifying compounds which modulate the activity of mutant B-Raf, said method comprising exposing cells containing heterologous DNA encoding mutant B-Raf, wherein said cells produce functional mutant B-Raf, to at least one compound or mixture of compounds or signal whose ability to modulate the activity of said mutant B-Raf is sought to be determined, and thereafter monitoring said cells for changes caused by said modulation. Such an assay enables the identification of modulators, such as agonists, antagonists and allosteric modulators, of mutant B-Raf. As used herein, a compound or signal that modulates the activity of mutant B-Raf refers to a compound that alters the activity of mutant B-Raf in such a way that the activity of mutant B-Raf on a target thereof, such as MEK, is different in the presence of the compound or signal (as compared to the absence of said compound or signal).

Cell-based screening assays can be designed by constructing cell lines in which the expression of a reporter protein, i.e. an easily assayable protein, such as β-galactosidase, chloramphenicol acetyltransferase (CAT) or luciferase, is dependent on the activation of a mutant B-Raf substrate. For example, a reporter gene encoding one of the above polypeptides may be placed under the control of an response element which is specifically activated by MEK or MAPK. Such an assay enables the detection of compounds that directly modulate mutant B-Raf function, such as compounds that antagonise phosphorylation of MEK by mutant B-Raf, or compounds that inhibit or potentiate other cellular functions required for the activity of mutant B-Raf. Cells in which wild-type, non-mutant B-Raf is present provide suitable controls.

Alternative assay formats include assays which directly assess proliferative responses in a biological system. The constitutive expression of unregulated mutant B-Raf results in an proliferative phenotype in animal cells. Cell-based systems, such as 3T3 fibroblasts, may be used to assess the activity of potential regulators of mutant B-Raf.

In a preferred aspect of this embodiment of the invention, there is provided a method for identifying a lead compound for a pharmaceutical useful in the treatment of disease involving or using an inflammatory response, comprising:

incubating a compound or compounds to be tested with mutant B-Raf and MEK, under conditions in which, but for the presence of the compound or compounds to be tested, mutant B-Raf directly or indirectly causes the phosphorylation of MEK with a reference phosphorylation efficiency;

determining the ability of mutant B-Raf to cause the phosphorylation, directly or indirectly, of MEK in the presence of the compound or compounds to be tested; and selecting those compounds which modulate the ability of mutant B-Raf to phosphorylate MEK with respect to the reference phosphorylation efficiency.

In a further preferred aspect, the invention relates to a method for identifying a lead compound for a pharmaceutical, comprising the steps of:

providing a purified mutant B-Raf molecule;

incubating the mutant B-Raf molecule with a substrate known to be phosphorylated by mutant B-Raf and a test compound or compounds; and identifying the test compound or compounds capable of modulating the phosphorylation of the substrate.

A substrate for mutant B-Raf phosphorylation is MEK. Preferably, therefore, MEK is used as a substrate to monitor compounds capable of modulating mutant B-Raf kinase activity. This allows the person skilled in the art to screen directly for kinase modulators. Preferably, kinase modulators are kinase (mutant B-Raf) inhibitors.

In a preferred embodiment, the activity of B-Raf may be measured according to the following protocol:

1. Cells are solubilized in lysis buffer (150 mM NaCl, 25 mM HEPES [pH 7.3], 1 mM sodium orthovanadate, 1% Triton X-100, protease inhibitors, 0.5 mM dithiothreitol).
2. The lysate is incubated on ice for 10 min and centrifuged at 14,000 3 g for 10 min, and the supernatant incubated with polyclonal anti-B-Raf antibody and then with protein G-Sepharose at 4° C. for 1 h.
3. The immunoprecipitates are washed twice with lysis buffer, and the kinase reaction carried out at 30° C. for 10 min in kinase buffer (0.2 mM ATP, 30 mM $MgCl_2$, 2 mM $MnCl_2$, 40 mM sodium β-glycerophosphate, 0.2 mM sodium orthovanadate, 2 mM okadaic acid, 0.2% β-mercaptoethanol) with 1 mg of purified recombinant MEK1 added as the substrate.
4. After MEK1 activation, 15 mCi of $[\gamma\text{-}32P]$ATP and 1 mg of kinase-defective (K52R) Erk are added as the substrate for an additional 2 min. The reaction is terminated by the addition of sample buffer, the mixture was boiled for 5 min, and the proteins separated by SDS-PAGE.
5. The gel proteins are transferred to a polyvinylidene difluoride membrane, on which the amount of radiolabeled K52R Erk is quantitated by a PhosphorImager.
6. For the calculations of B-Raf activity, the amount of B-Raf protein on the same membrane is determined by probing the membrane with $^{125}$I-labeled goat anti-mouse IgG following mouse monoclonal anti-B-Raf blotting.
7. The assay can be repeated in the presence or absence of compound(s) to be tested.

Optionally, the test compound(s) identified may then be subjected to in vivo testing to determine their effects on a mutant B-Raf signalling pathway, for example as set forth in the foregoing embodiment.

As used herein, "mutant B-Raf activity" may refer to any activity of mutant B-Raf, including its binding activity, but in particular refers to the phosphorylating activity of mutant B-Raf Accordingly, the invention may be configured to detect the phosphorylation of target compounds by mutant B-Raf, and the modulation of this activity by potential therapeutic agents.

Examples of compounds which modulate the phosphorylating activity of mutant B-Raf include dominant negative mutants of B-Raf itself. Such compounds are able to compete for the target of mutant B-Raf, thus reducing the activity of mutant B-Raf in a biological or artificial system. Thus, the invention moreover relates to compounds capable of modulating the phosphorylating activity of mutant B-Raf.

Compounds which influence the activity of mutant B-Raf may be of almost any general description, including low molecular weight compounds, including organic compounds which may be linear, cyclic, polycyclic or a combination thereof, peptides, polypeptides including antibodies, or proteins. In general, as used herein, "peptides", "polypeptides" and "proteins" are considered equivalent.

Many compounds according to the present invention may be lead compounds useful for drug development. Useful lead compounds are especially antibodies and peptides, and particularly intracellular antibodies expressed within the cell in a gene therapy context, which may be used as models for the development of peptide or low molecular weight therapeutics. In a preferred aspect of the invention, lead compounds and mutant B-Raf or other target peptides may be co-crystallised in order to facilitate the design of suitable low molecular weight compounds which mimic the interaction observed with the lead compound.

Crystallisation involves the preparation of a crystallisation buffer, for example by mixing a solution of the peptide or peptide complex with a "reservoir buffer", preferably in a 1:1 ratio, with a lower concentration of the precipitating agent necessary for crystal formation. For crystal formation, the concentration of the precipitating agent is increased, for example by addition of precipitating agent, for example by titration, or by allowing the concentration of precipitating agent to balance by diffusion between the crystallisation buffer and a reservoir buffer. Under suitable conditions such diffusion of precipitating agent occurs along the gradient of precipitating agent, for example from the reservoir buffer having a higher concentration of precipitating agent into the crystallisation buffer having a lower concentration of precipitating agent. Diffusion may be achieved for example by vapour diffusion techniques allowing diffusion in the common gas phase. Known techniques are, for example, vapour diffusion methods, such as the "hanging drop" or the "sitting drop" method. In the vapour diffusion method a drop of crystallisation buffer containing the protein is hanging above or sitting beside a much larger pool of reservoir buffer. Alternatively, the balancing of the precipitating agent can be achieved through a semipermeable membrane that separates the crystallisation buffer from the reservoir buffer and prevents dilution of the protein into the reservoir buffer.

In the crystallisation buffer the peptide or peptide/binding partner complex preferably has a concentration of up to 30 mg/ml, preferably from about 2 mg/ml to about 4 mg/ml.

Formation of crystals can be achieved under various conditions which are essentially determined by the following parameters: pH, presence of salts and additives, precipitating agent, protein concentration and temperature. The pH may range from about 4.0 to 9.0. The concentration and type of buffer is rather unimportant, and therefore variable, e.g. in dependence with the desired pH. Suitable buffer systems include phosphate, acetate, citrate, Tris, MES and HEPES buffers. Useful salts and additives include e.g. chlorides, sulphates and other salts known to those skilled in the art. The buffer contains a precipitating agent selected from the group consisting of a water miscible organic solvent, preferably polyethylene glycol having a molecular weight of between 100 and 20000, preferentially between 4000 and 10000, or a suitable salt, such as a sulphates, particularly ammonium sulphate, a chloride, a citrate or a tartarate.

A crystal of a peptide or peptide/binding partner complex according to the invention may be chemically modified, e.g. by heavy atom derivatization. Briefly, such derivatization is achievable by soaking a crystal in a solution containing heavy metal atom salts, or a organometallic compounds, e.g. lead chloride, gold thiomalate, thimerosal or uranyl acetate, which is capable of diffusing through the crystal and binding to the surface of the protein. The location(s) of the bound heavy metal atom(s) can be determined by X-ray diffraction analysis of the soaked crystal, which information may be used e.g. to construct a three-dimensional model of the peptide.

A three-dimensional model is obtainable, for example, from a heavy atom derivative of a crystal and/or from all or part of the structural data provided by the crystallisation.

Preferably building of such model involves homology modelling and/or molecular replacement.

The preliminary homology model can be created by a combination of sequence alignment with any RAF kinase the structure of which is known, secondary structure prediction and screening of structural libraries. For example, the sequences of mutant B-Raf and a candidate peptide can be aligned using a suitable software program.

Computational software may also be used to predict the secondary structure of the peptide or peptide complex. The peptide sequence may be incorporated into the mutant B-Raf structure. Structural incoherences, e.g. structural fragments around insertions/deletions can be modelled by screening a structural library for peptides of the desired length and with a suitable conformation. For prediction of the side chain conformation, a side chain rotamer library may be employed.

The final homology model is used to solve the crystal structure of the peptide by molecular replacement using suitable computer software. The homology model is positioned according to the results of molecular replacement, and subjected to further refinement comprising molecular dynamics calculations and modelling of the inhibitor used for crystallisation into the electron density.

Kinase Activation Studies

Figure 1B:
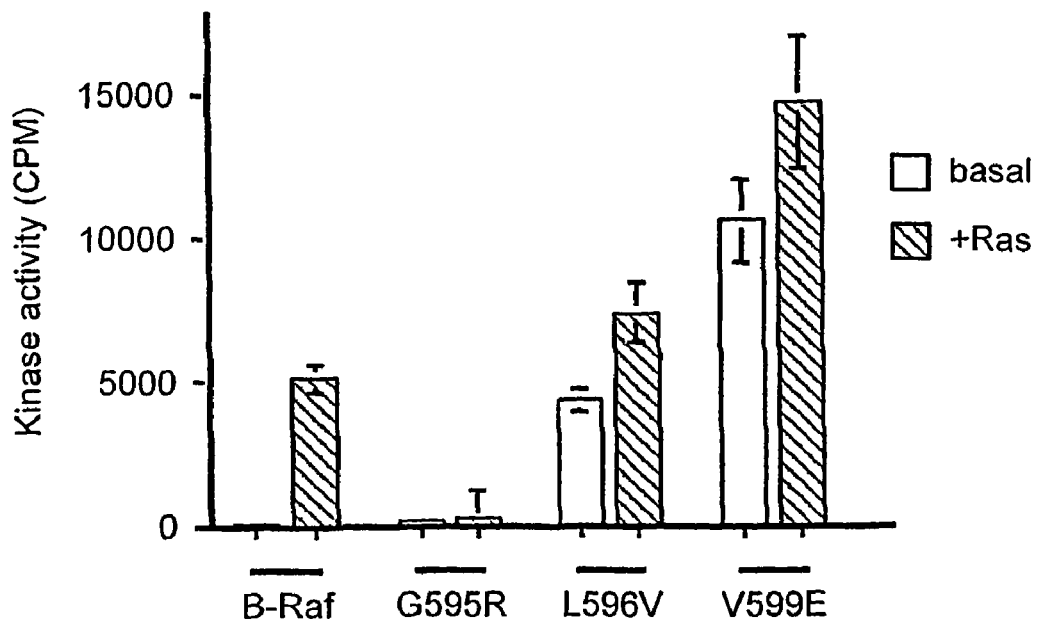
FIG. 1B: B-Raf activity assays. The kinase activity of B-Raf was measured in an immunoprecipation kinase cascade assay, using MBP as the final substrate. The activity is shown as number of counts incorporated into MBP. The assay was performed in triplicate and the average is shown, with error bars to represent deviations from the mean. Both the basal kinase activity (open bars) and the $^{V12}$Ras stimulated kinase activities are shown.

Constitutively active kinase mutants are valuable research tools in the elucidation of signalling pathways and the development of therapeutic agents which modulate such pathways. The activity of five of the mutants according to the invention has been examined. These are G463V, G468A, G595R, L596V and V599E. To examine the activity of the mutants, myc-epitope tagged versions of B-Raf are transiently expressed in COS cells. To examine the activity of this exogenously expressed B-Raf, the protein is immunoprecipitated using the myc-tag and examined in a kinase cascade assay, using bacterially produced GST-MEK, GST-ERK and myelin basic protein (MBP) as sequential substrates (Marais et al (1997); J. Biol. Chem. 272: 4378-83). B-Raf has high levels of basal kinase activity, being significantly more active in the absence of activators than either Raf-1 or A-Raf (Marais et al (1997); J. Biol. Chem. 272: 4378-83). Moreover, whereas Raf-1 and A-Raf require both oncogenic Ras ($^{V12}$Ras) and activated Src to stimulate their activity fully, B-Raf is fully activated by co-expression with $^{V12}$Ras alone. The effect these mutations have on both the basal activity of B-Raf and on the activity stimulated by $^{V12}$Ras is therefore assayed. Compared to wild-type B-Raf, $^{G463V}$B-Raf, $^{G468A}$B-Raf $^{L596V}$B-Raf and $^{V599E}$B-Raf all possess strongly elevated basal kinase activity (FIG. 1A, 1B). By comparison, $^{G595R}$B-Raf has reduced basal activity compared to the wild-type protein (FIG. 1A). Similar results are observed in vivo. All five mutants are stimulated by oncogenic Ras ($^{V12}$Ras). However, the fold activation for each of the mutants is reduced compared with wild-type B-Raf (See FIG. 1A, B) and is particularly small in the case of $^{V599E}$B-Raf. However, since the basal activity of each of $^{G463V}$B-Raf, $^{G468A}$B-Raf, $^{L596V}$B-Raf and $^{V599E}$B-Raf is higher than the wild-type protein, then absolute levels of activity seen are higher in each case in the presence of $^{V12}$Ras than for the wild-type protein. Interestingly, $^{G595R}$B-Raf is also stimulated by $^{V12}$Ras, but the activation was very weak, probably due to the low starting levels.

Figure 2:
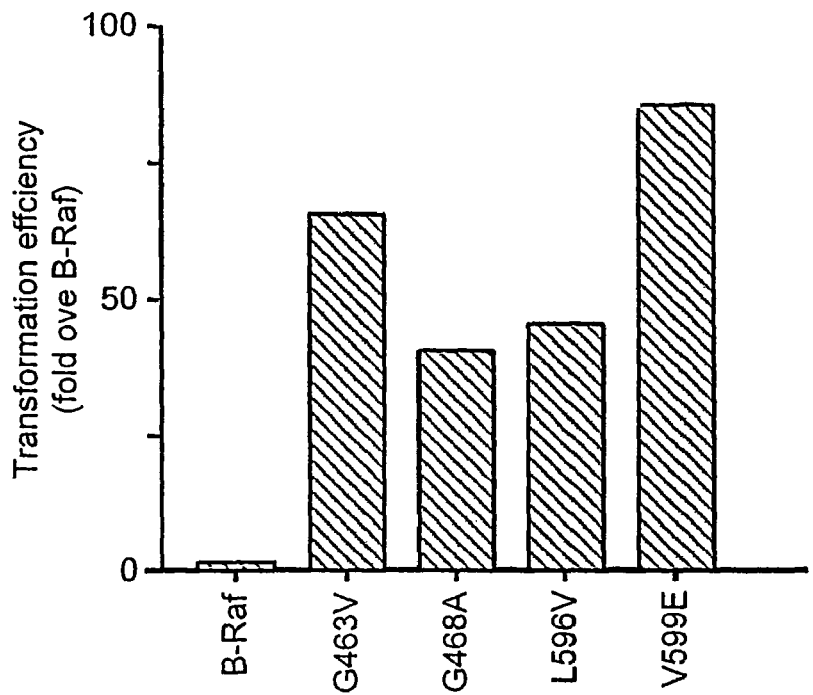
FIG. 2: Transformation of NIH3T3 cells by B-Raf and activating mutants. The cells were transfected with the indicated constructs and the number of colonies was determined. The results are the average of at least three assays. The number of colonies relative to the number induced by B-Raf is shown.

The ability of each of the activated mutants to transform NIH3T3 cells is also examined. In this assay, wild-type B-Raf transforms cells at very low efficiency (~0.02% of the number of colonies seen with $^{V12}$Ras). However, as shown in FIG. 2, the each of the activated mutants transforms NIH3T3 cells 40 to 85 fold more efficiently than does wild-type B-Raf.

The extent of dependence of the growth of cells that contain the B-Raf mutants on the Ras/MEK pathway is investigated. For these studies, two assays are used. The first is to test whether their growth is suppressed by micro-injection of the monoclonal antibody Y13-259, an antibody that neutralises the activity of cellular Ras. The results are shown in Table 2. The data are divided into three groups. The first group have wild-type B-Raf and are their growth is inhibited (40-100%) by Y13-259. The second group have activating mutations in B-Raf and their growth was not inhibited (<15%) by Y13-259. The third group (only one case) contains a cell which has both an activating Ras and an activating B-Raf mutation. Intriguingly, the growth of this cell line was inhibited by Y13-259, but this may be because the growth is dependent on both Ras and B-Raf.

The second approach is to examine the effects of the compound U0126, an inhibitor of MEK1/2, the only known substrates for B-Raf. These results demonstrate that treatment of cells that have activating mutations in B-Raf results in suppression of cell proliferation when MEK activity is suppressed indicating that the activation of cell signalling by activated mutants of B-Raf is a therapeutic target. See Table 3.

Taken together, the above data demonstrate that
1. There are two classes of B-Raf mutation in human tumours, activating and inactivating mutations.
2. The activated versions of B-Raf are able to transform NIH3T3 cells and so are can be defined as oncogenes.
3. Human tumour cell lines that express activated B-Raf protein are not sensitive to Y13-259, a Ras neutralising antibody, indicating that their growth is not dependent on Ras proteins and so are unlikely to respond to compounds that target the Ras proteins. This indicates that the activating mutants may overcome the requirement for Ras signals in tumour cells.
4. However, their activity is suppressed by the compound U0126, indicating that their growth is dependent on the activity of this pathway and therefore likely to respond to therapeutic agents that target B-Raf activity.
5. Since some of the mutations are in the phosphate-binding loop of the kinase domain (G463, G465, G468) and these amino acids are conserved in all kinases, these mutations represent a global and convenient mechanism to activate kinases. This has important implications in the screening for therapeutic agents.

The invention accordingly provides a constitutively active kinase comprising a mutation in the phosphate binding loop thereof selected from the group consisting of mutations at one or more positions corresponding to positions 463, 465 and 468 of B-Raf.

Preferably, the mutation is at one or more of positions 463 and 468.

Most preferred are G463V and G468A.

Many kinases are identified to be associated with a specific disease, but their mechanisms of activation may not always be fully understood. Constitutively activated mutants thereof as described herein provide a reagent that can be used to screen for inhibitors without having to first elucidate their mechanism of activation.

Exemplary kinases include other kinases on the MAP kinase pathway, such as MEK and ERK and the other MAP kinase pathways, such as p38, JNK and their upstream kinases. Although something is known about their activation mechanisms, for some it is not known how to activate them by direct mutation. The present invention provides activated mutants of said kinases screening purposes. Moreover, kinases that are downstream of the MAP kinases, such as p90Rsk, nmk, etc., can also be activated. Although alternative activation mechanisms are known, mutation may be a preferable route in screening assays.

The invention also encompasses certain known kinases which have no known activation mechanism, such as Lkb1, which is involved in Putzjegers syndrome; and kinase PDK1 which may be constitutively active, but which can be further activatable for drug screening. This kinase is involved in insulin signalling, so may be a useful target for diabetes. Also involved in type II diabetes is the AMP-activated kinase, which again is activated by phosphorylation and is therefore amenable to activation by mutation.

Therefore, the invention provides a method for screening one or more compounds for an inhibitory effect on a kinase, comprising
(a) preparing a mutant-kinase comprising an amino acid substitution, deletion or insertion at one or more of positions 463, 465 or 468 as detailed above;
(b) exposing the mutant kinase to said one or more compounds in the presence of a kinase substrate; and
(d) determining the ability of the kinase to phosphorylate the substrate in the presence of the one or more compounds.

The phosphorylating activity of the kinase in the presence of the test compound(s) is advantageously compared to its activity in the absence of the compound(s); a reduction in the basal activity of the mutant kinase is indicative of inhibition of the kinase by the compound(s). For multiple assays, a reference level of phosphorylation may be determined for a particular assay, and used as a basis for comparison.

Preferably, the kinase is a Raf protein kinase; advantageously, it is B-Raf.

Conversely, constitutively repressed mutants such as B-Raf G595R are useful in screening for activators of a kinase.

Validation of bRAF as a drug target.

Figure 3A:
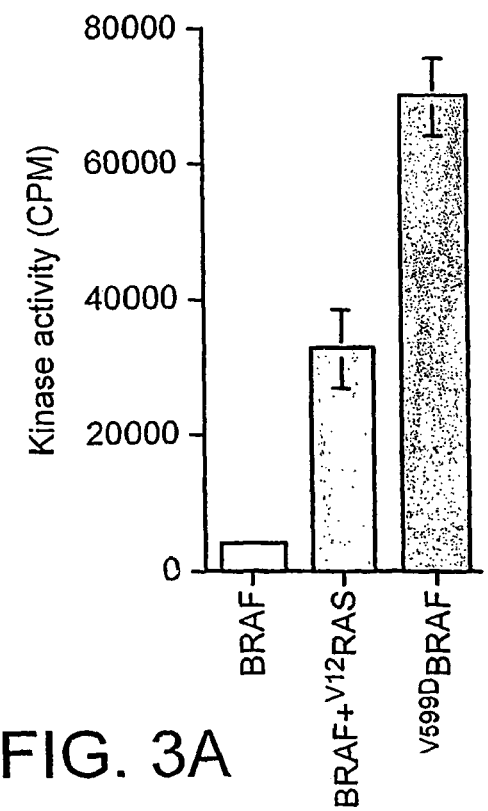
FIG. 3A. V599D is an activating mutation in BRAF. BRAF or $^{V599D}$BRAF were expressed alone, or together with oncogenic Ras as indicated. The activity of the BRAF proteins were determined using an immunoprecipitation kinase cascade assay in which immunoprecipitated BRAF is used to sequentially activate MEK and ERK. The activation of ERK is determined using myelin basic protein and [$^{32}$P]-γATP as substrates.
Figure 3B:
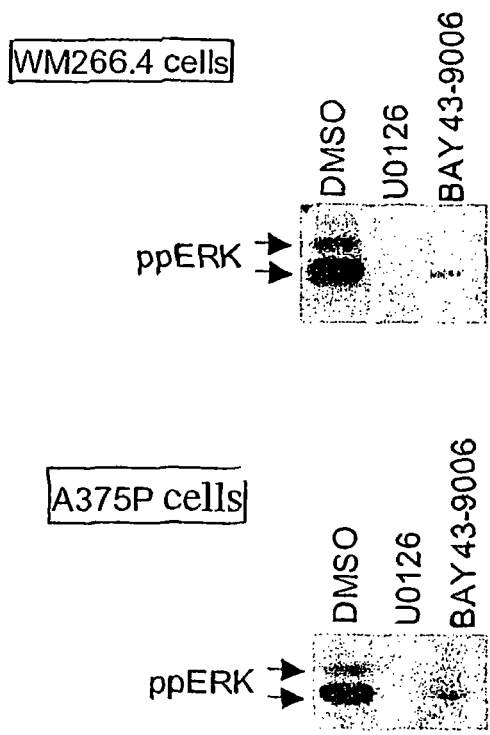
FIG. 3B. Inhibition of ERK in melanoma cell lines using pharmacological reagents. WM266.4 or. A375P cells were treated with 10 μM U0126, 10 μM BAY 43-9006 or DMSO as a control. Equivalent amounts of cellular proteins were resolved on SDS-gels and the levels of active ERK were determined using the ppERK antibody.

In order to validate BRAF as a target in cancer, it is first tested whether the growth of cells that express activated, mutant forms of BRAF required the RAF-MEK-ERK signaling pathway for growth. To this end, melanoma and colorectal cell lines that harbour mutations in the BRAF gene are treated with pharmacological agents that block signaling through this pathway. Two compounds are tested. One is the compound U0126, which is a MEK inhibitor and which therefore uncouples RAF-ERK signaling in cells (Sebolt-Leopold et al., 1999). BAY 43-9006 os also tested. This is an inhibitor of RAF proteins (Lyons et al., 2001). The ability of these compounds to block ERK activity was tested in the melanoma cell line WM266.4, which have substitution of an aspartic acid for valine at position 599 of the BRAF gene. This is an activating mutation (FIG. 3A). These cells also have elevated basal kinase activity as judged using an antibody (pERK) that only binds to the doubly phosphorylated, activated version of ERK. When the ppERK antibody is used to Western blot WM266.4 cells, a strong signal is seen in the region of 42-44 kDa, indicating that ERK has elevated basal kinase activity in these cells (FIG. 3B). However, when the cells are treated with U0126, or Bay 43-9006, ERK activity is strongly suppressed (FIG. 3B). Similar results were obtained using A375 cell, a melanoma cell line that harbours a V599E mutation in the BRAF gene (Davies et al., 2002). These data demonstrate that that RAF and MEK signaling is required for the maintenance of the elevated ERK activity in these cells.

Figure 4:
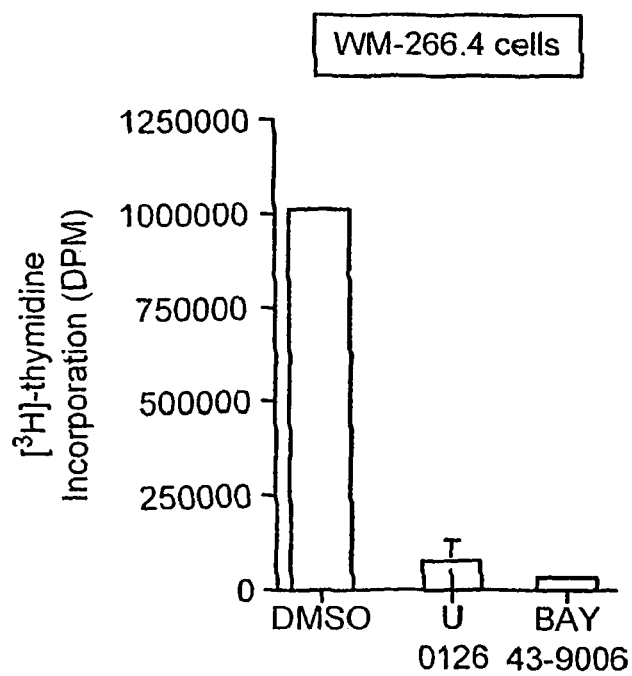
FIG. 4. Inhibition of cell growth by pharmacological agents. WM-266.4 cells were incubated in the presence of U0126 (10 μM) or BAY 43-9006 (10 μM) or the vehicle control (DMSO). After 48 hours, DNA synthesis was determined by incubating the cells with [$^3$H]-thymidine and the levels of thymidine incorporated into the cellular DNA was determined.

We next tested what effect BAY 43-9002 had on the growth of WM266.4 cells and found that this compound blocked the growth of these cells with an IC50 of ~6.1 µM (Table 4). BAY 43-9006 also blocked the growth of colo 829 cells and of BE cells in the low micro-molar range (Table 4). Colo 829 cells are a melanoma cell line that harbours a V599E mutation in the BRAF gene and BE cells are a colorectal line that harbour a G463 mutation in the BRAF gene (Davies et al., 2002). As we have shown, both of these mutations are activating (Davies et al., 2002). Finally, we tested the effects of these inhibitors on DNA synthesis. Incubation of WM-266.4 cells with 10 µM U0126, or 10 µM BAY 43-9006 strongly suppressed DNA synthesis in these cells (FIG. 4). These data demonstrate that ERK activation and proliferation in cells that harbour activating mutations in the BRAF gene are dependent on RAF and MEK activities.

Figure 5A:
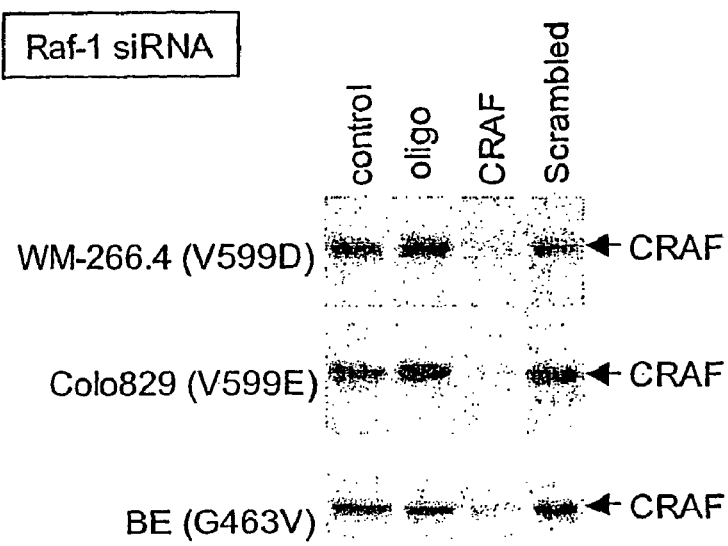
FIG. 5A. CRAF expression is suppressed by siRNA. WM-266.4, Colo 829 or BE cells were treated with a CRAF specific siRNA probe (CRAF), the scrambled siRNA probe (scrambled), oligofectamine (oligo) or untreated (control). The cells were incubated for 24 hours and the levels of CRAF protein was determined by Western blotting.
Figure 5B:
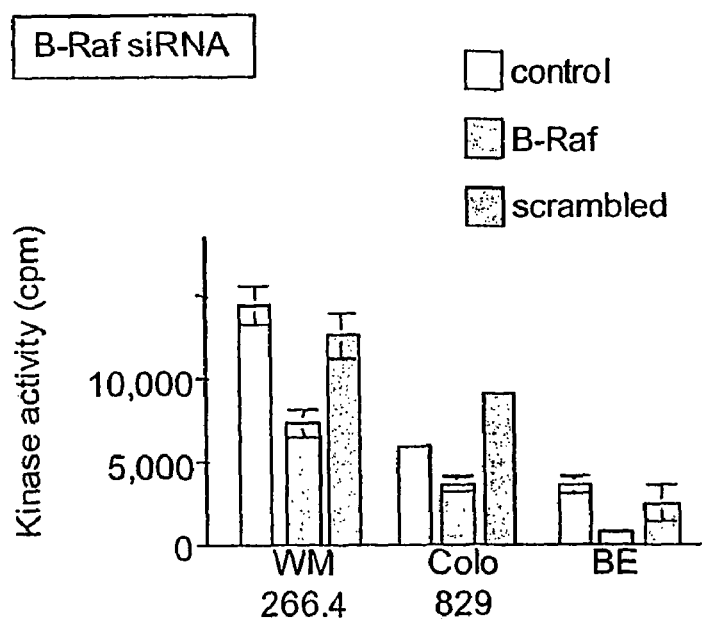
FIG. 5B. BRAF expression is suppressed by siRNA. WM-266.4, Colo 829 or BE cells were treated with a BRAF specific siRNA probe, the scrambled siRNA probe, or were left untreated as shown. The cells were incubated for 24 hours and the levels of BRAF activity were tested using an immunoprecipitation kinase assay MEK and ERK as sequential assays. The activity of ERK was determined using MBP and [$^{32}$P]-γATP as substrates.

There are three RAF genes in mammalian cells, CRAF (also called RAF-1), ARAF and BRAF. U0126 is a MEK inhibitor and therefore will not be able to distinguish CRAF from BRAF or ARAF signaling. Similarly, BAY 43-9006 can inhibit both CRAF and BRAF, so will not distinguish between the different RAF isoforms. Therefore, in order to determine which RAF isoform was signaling to ERK in WM266.4, cells were treated with small interference RNA (siRNA) probes that are selective for the individual RAF isoforms. WM266.4 cells were treated with siRNA probes designed to be specific for BRAF, or CRAF, or a scrambled control that should not recognize either isoform. The efficiency of the recognition for CRAF was determined by Western blotting. Treatment of WM266.4 cells with a siRNA probe specific for CRAF resulted in strong suppression of CRAF expression (FIG. 5A). Similar results were observed in Colo 829 cells and BE cells (FIG. 5A). When WM-266.4 cells were treated with a BRAF specific siRNA probe, BRAF activity in the cells was strongly suppressed, but no suppression was observed when the cells were treated with the scrambled control (FIG. 5B). Similar results were observed in Colo 829 and BE cells (FIG. 5B).

Figure 6:
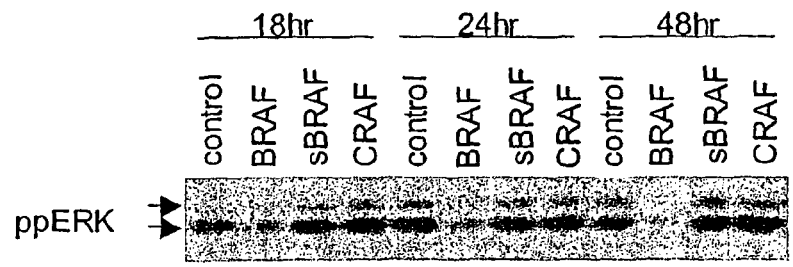
FIG. 6. Ablation of BRAF, but not CRAF blocks ERK activity in melanoma cells. WM-266.4 or Colo 829 cells were treated with a BRAF specific siRNA probe (BRAF), or the scrambled control (sBRAF), or a CRAF specific probe (CRAF), or its scrambled control (sCRAF), or oligofectamine (oligo) or left untreated (control) as indicated. The cells were incubated for the times indicated, and the Colo 829 cells were treated for 24 hours. The levels of ERK activity in equivalent amounts of cell extract was determined by Western blotting with the ppERK antibody.
Figure 6:
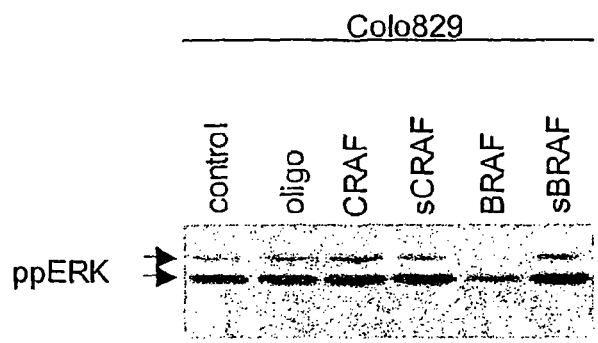

The above data show that siRNA can be used to selectively suppress expression of the BRAF and CRAF proteins. We therefore examined how ablation of each of these proteins affected ERK activity in these cells. When siRNA was used to ablate BRAF protein expression in WM-266.4, ERK activity was suppressed in a time-dependent manner (FIG. 6). By contrast, ablation of CRAF expression or treatment with the scrambled siRNA probes did not affect ERK activity (FIG. 6). Similar results were obtained in Colo 829 cells (FIG. 6). These results demonstrate that BRAF is the major isoform that signals to ERK in melanoma cells that express activated BRAF proteins. CRAF does not appear to signal to basal ERK activity in these cells.

Figure 7:
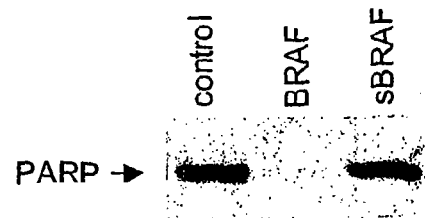
FIG. 7. Ablation of BRAF, but not CRAF induces apoptosis in melanoma cells. WM-266.4 cells were treated with a BRAF specific siRNA probe (BRAF), or the scrambled control (sBRAF), or a CRAF specific siRNA probe (CRAF), or U0126, or DMSO (oligo) or left untreated (control) as indicated. The cells were incubated for 96 hours and the cell cycle profile was analysed by FACS, or PARP expression was examined by Western blotting.

Finally, we examined how BRAF ablation affected cell growth, examining the effects on apoptosis in WM-266.4 cells. For these studies, the cells were fixed in 70% ethanol, stained with propridium iodide and their cell cycle profiles were examined by fluorescent activated cell sorting (FACS). Using this analysis, the apoptotic cells, appear in the sub-G1 peak. In these cells, spontaneous apoptosis is very low, with less than 1% of the cell Reagent Validation appearing in the sub-G1 peak (FIG. 7, table 5). When the cells are treated with U0126, the proportion of cells in the sub-G1 peak is significantly increased (~3.5%; FIG. 7, Table 5). Similarly, ablation of BRAF expression by use of siRNA also increases the number of cells in the sub-G1 peak, whereas ablation of CRAF or treatment with the scrambled control did not. We also examined PARP cleavage, a marker of the induction of apoptosis. Treatment of the cells with BRAF siRNA induced cleavage of PARP, whereas the scrambled control did not. These data demonstrate that when mutant BRAF protein is ablated in melanoma cell lines, apoptosis is induced.

In summary, these results demonstrate that in melanoma cell lines that express activated mutants of BRAF, signaling through RAF and MEK is required for ERK activation and for cell growth. BRAF, rather than CRAF appears to be the major RAF isoform that stimulates ERK activity, and appears to protect the cells from apoptosis. These data suggests that BRAF is an important therapeutic target in cells that rely on BRAF signaling for growth and protection from apoptosis.

Development of High-Throughput Screening Assay

Figure 8:
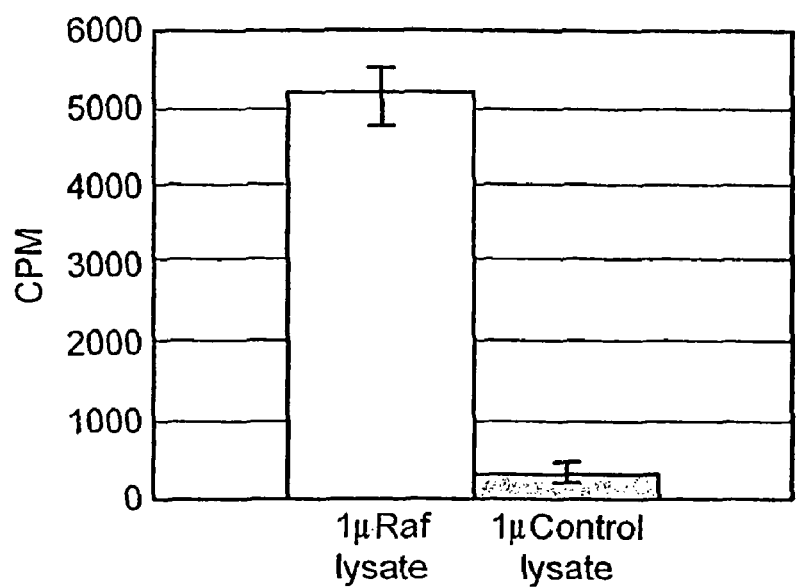
FIG. 8. B-Raf and GST -MKKI activity validation. Assay performed using WTS 1 B-Raf lysate (Batch A), GST MKK1 (6.5 μg/ml) and ERK2 (kinase competent, 100 μg/ml) to measure $^{33}$P-γ-phosphate incorporation into MBP (0.3 mg/ml). Data shown are mean ±SD of triplicate determinations.

A HTS assay has been developed for the B-raf mutant V599E. In order to validate results, -Raf-expressing lysate and GST-MKK1 reagents were activity checked by conducting a standard coupled assay employing GST-ERK2 (kinase competent) and measuring $^{33}$P-$\gamma$-phosphate incorporation into myelin basic protein (MBP). As shown in FIG. 8, in the presence of the B-Raf lysate a 16-fold increase in signal was observed compared to the control (non-expressing) lysate.

Assay Platform Validation

Option 1: Coupled Kinase Assay in Glutathione FlashPlate

Principle of Platform: GST-tagged substrate (ERK-2) is captured onto the scintillant-embedded walls of a flashplate via a glutathione coating. The incorporation of $^{33}$P-$\gamma$-phosphate into substrate should result in a measurable scintillation signal.

Figure 9:
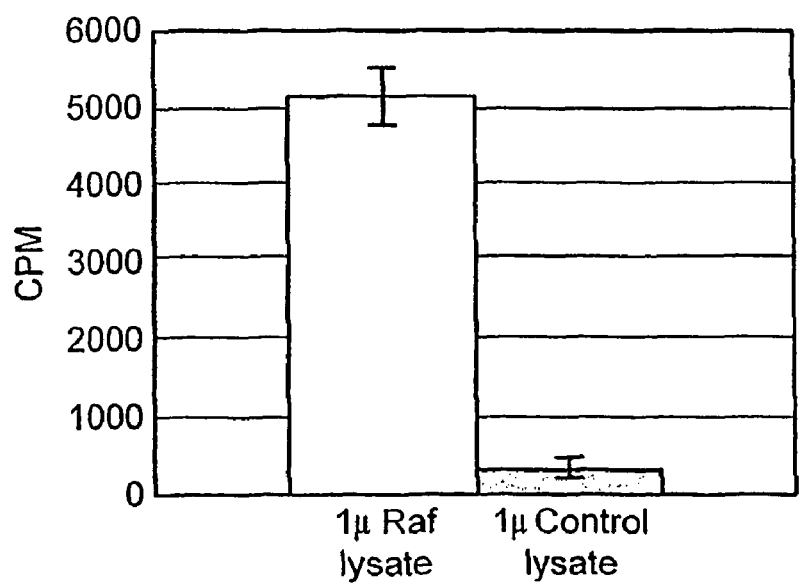
FIG. 9. Assessment of Filter Plate and FlashPlate Radiometric Assay Platform. Assay performed using WTS1 B-Rafllysate (Batch A) and GST MKK1(6.5 μg/ml) to measure $^{33}$P-γ-phosphate incorporation into GST-kdERK2(100 μg/ml). Data shown are mean ±SD of triplicate -determinations.

The possibility of measuring the incorporation of $^{33}$P-$\gamma$-phosphate into GST-kinase dead ERK2 (GST-kdERK2) as an output of B-Raf activity was evaluated in a glutathione flashplate assay. FIG. 9 demonstrates that, using the conditions transferred from the reagent validation exercise, we were unable to detect the B-Raf-dependent incorporation of $^{33}$P into GST-kdERK2 using this platform. A standard p81 filter plate assay also proved unsuccessful. As a consequence of the amplification characteristics of this cascade assay, maintaining an assay signal in the absence of the final assay step (ie. ERK2 phosphorylation of MBP) would most likely require significantly increased levels of each the remaining constituents. It was therefore deemed appropriate to assess the antibody-based platform prior to embarking upon the reagent-costly exercise of B-Raf, MKKI and ERK2 titrations in this radiometric platform.

Option 2: Coupled Kinase Assay in DELFIA Format

DELFIA (Dissociation-Enhanced Lanthanide Fluorescence ImmunoAssay) assay involves the measurement of ERK2 phosphorylation via binding of a phospho-specific antibody. The coupled kinase assay B-Raf/GST-MKKI/GST-kdERK2 generates phosphorylated GST-kdERK2. An anti-GST-coated plate is used to capture the GST-kdERK2. A primary antibody is added that specifically detects ERK2 phosphorylated on Threonine and Tyrosine. A Europium {Eu}-labelled secondary antibody is then added. In the presence of Enhancement Solution, the Eu-label dissociates from the antibody absorbing at 335 nm and allowing fluorometric detection at an emission wavelength of 620 nm.

Figure 10:
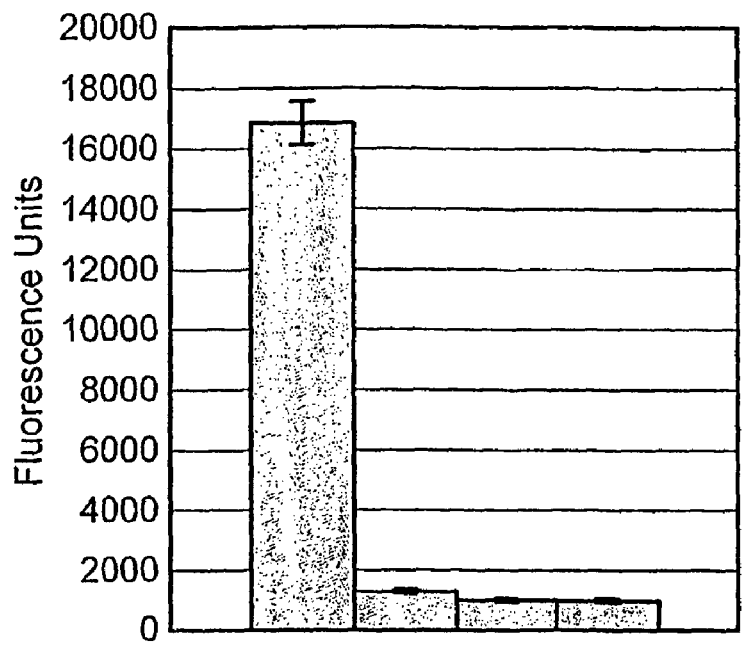
FIG. 10. Assessment of DELFIA non-radiometric assay plafform. 100ng GST-kdERK2 was pre-bound to each well followed by the addition of B-Raf lysate (Batch A), GST-MKKI (6.5 g/ml) and ATP (500 M). Data shown are meanSD of triplicate determinations. The data bars show, from left to right, 1: Raf+MKK1+ERK; 2: Control+MKK1+ERK; 3: Raf+ERK(no MKK1); 4: Raf+MKK1(no ERK).
Figure 11:
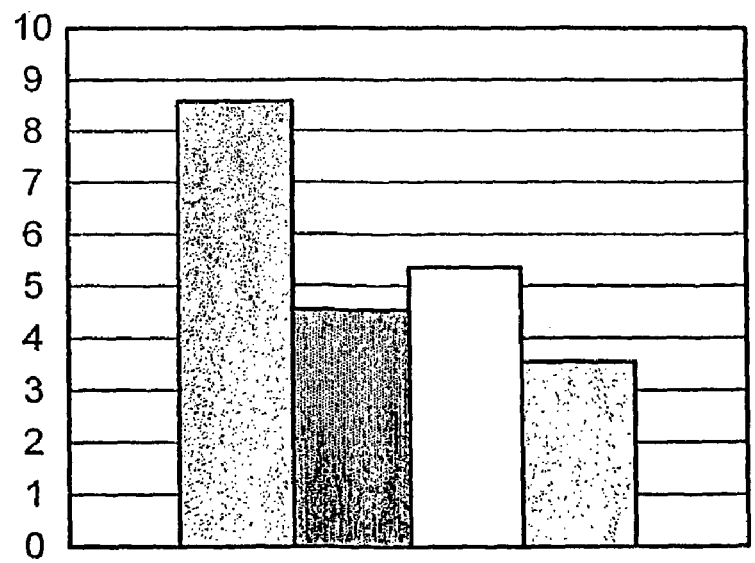
FIG. 11. Titration of anti-phospho-ERK2 in DELFIA Assay. 100ng GST-kdERK2 was pre-bound to the well followed by the addition of B-Raf lysate (Batch A), GST-MKKI (6.51 lg/ml) and ATP (500 M). Data shown are mean of duplicate determinations. The data bars show, from left to right, 1: ERK: 3,000, EU: 1,000; 2: ERK: 9,000, Eu: 1,000; 3: ERK 12,000, Eu: 1,000; 4: ERK: 20,000, Eu: 1000. The Y axis measure signal:background ratio.
Figure 12:
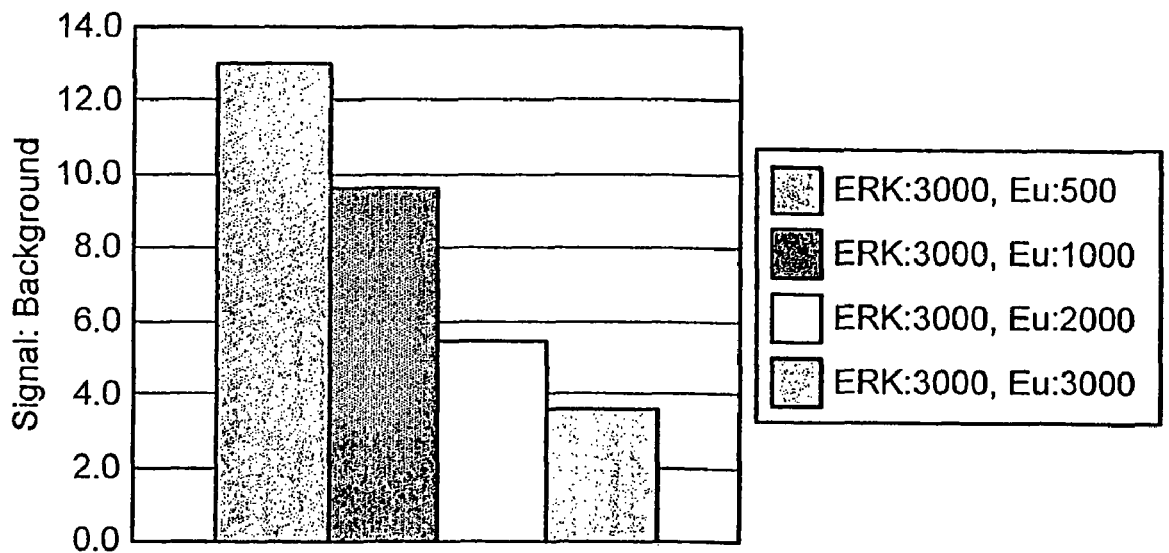
FIG. 12. Titration of Europium-labelled Secondary antibody in DELFIA Assay. 100 ng GST-kdERK2 was pre-bound to the well followed by the addition of B-Raf lysate (Batch A), GST-MKK1 (6.5 µg/ml) and ATP (500 µM). Data shown are mean of duplicate determinations.

The B-Raf assay was assessed in this platform employing a combination of kinase assay conditions from the reagent validation exercise and standard DELFIA assay conditions. FIG. 10 shows that in the presence of the B-Raf lysate a 12.2-fold increase in signal was observed compared to the control (non-expressing) lysate. The signal observed was entirely dependent upon the presence of all three enzyme/substrate components.

Based on preliminary experiments, the DELFIA platform was selected for development.

Kinase Assay Development

B-Raf Lysate

Three batches of B-Raf lysate have been used throughout the procedure. Batch A was employed to establish the DELFIA assay platform. Batch B has been used during assay development. For Batches B and C an approximate linear relationship between lysate quantity and level of signal attained was evident between 0.025 to 0.1 µl per well. The final quantities selected for each batch were based upon attaining a sufficient window of signal within the linear range. As a result of these assessments, Batch A was used at 1 µl/well [96-well] and Batches B and C (screening) have been used at 0.1 µl/well [96-well] and 0.05 µl/well [384-well].

Optimisation of Antibody Levels

Initial concerns regarding the possible competition of ERK2 and MKKI (both GST-tagged) for glutathione binding sites resulted in early development assays being conducted using a 'pre-binding protocol'.

These conditions were as follows:

Pre-binding of 100 ng/well GST-k-dERK to 96-well Glutathione-coated plates.

Addition of B-Raf lysate (Batch A), MKK1 (6.5 µg/ml) and ATP 500 µM) in a final volume of 50 µM DKB (see Appendix I) and incubation at 30° C. for 1 hour.

This protocol was employed to optimise and economise the antibody load of the detection system. Titrations of both primary and secondary antibodies were conducted to assess the possibility of reducing antibody levels whilst maintaining a signal to background ratio of ≧10.1. FIGS. 4 and 5 indicate that 1:3000 and 1:1000 were the lowest concentrations acceptable for phosphoERK2 and Eu-Labelled antibodies respectively. All subsequent assays were therefore performed using these antibody concentrations.

Optimisation of MKK1 and ERK2 Levels

Figure 13:
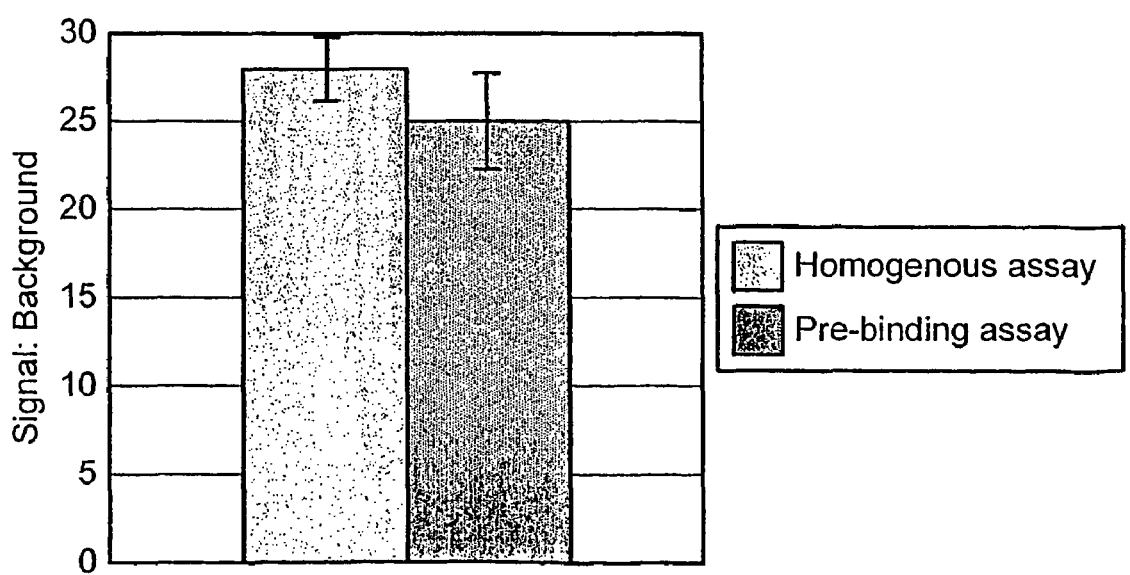
FIG. 13. Assessment of Homogenous Assay Protocol. The homogenous assay was performed in a 96-well plate using a 50 µl reaction volume containing a B-Raf lysate 9Batch B), 6.5 µg/ml GST-MKK1, 80 µg/ml GST-kdERK2 and 500 µM ATP. Data shown are mean ±SD of triplicate determinations.

The ability to perform the enzyme component of this assay 'in solution' without a pre-binding step was investigated to enable titration of defined concentrations of both MKK1 and ERK2. In addition, the reduction of this assay into a single-step (homogeneous) mixing of reagents involved in the kinase would make it more amenable to HTS. FIG. 13 illustrates that the homogenous assay and the pre-binding protocol gave equivalent data. All subsequent assays were performed using the 'homogeneous' protocol.

Titration of ERK-2 whilst maintaining MKK1 levels indicated that maximum signal was attained at a ratio of ~12:1 (ERK2:MKK1). In an attempt to economise on reagents a matrix titration of these components was performed. Using 0.1 µl B-Raf (Batch B), the combination of 6. 5 µg/ml GST-MKK1 and 80 µg/ml GST-kdERK2 gave the maximal signal and although some reduction in the. Raf/MKK1 load was possible it was deemed appropriate to maintain the original ratio. This decision was taken with the knowledge that further assay parameter alterations (e.g. transfer to 384; reduction of ATP load, transfer to automation) may reduce the signal window further. All subsequent assays were, therefore, performed using 6.5 µg/ml GST-MKK1 and 80 µg/ml GST-kdERK2.

Effect of Temperature

The ability to run this assay at room temperature would significantly simplify the eventual HTS process. The assay signal at room temperature and 30° C. was therefore investigated. Based upon the results obtained, the signal-to-background ratio was acceptable at room temperature and all subsequent assays were carried out at room temperature.

Evaluation of Assay in 384-Well Plate Format

In an attempt to enhance throughput and minimise reagent usage during the screen, the performance of the assay in 384-well format was assessed. In this format the assay performed well and both standard (final of 50 µl) and reduced reagent volume (25 µl) assays returned highly acceptable signal to background ratios. All subsequent development experiments were performed in 384-format using 25 µl reaction volumes.

Optimisation of ATP Concentration

The ATP concentration of a kinase screening assay has the potential to influence the number and nature of inhibitory compounds identified. Definition of the ATP levels of such an assay is a balance of the following considerations:

employing ATP levels that enable a consistent, measurable window of assay signal employing ATP levels low enough to permit the identification of ATP-competitive inhibitors employing ATP levels sufficiently high such that weak ATP-competitive agents likely to be ineffective in the context of cellular ATP are less likely to be detected Kinase screening assays are usually performed at an ATP concentration relative to Km. The derivation of Km values for B-Raf and MKK1 necessitates the development of individual assays for each enzyme rather than the coupled assay developed herein. The development of such assays will undoubtedly facilitate a future understanding of the mode of action of any inhibitory compounds identified in the screening assay.

For the purposes of defining the ATP load of the screening assay, the concentration-dependence of the coupled assay was determined. The signal generated is maximal and half maximal at ~200 µM and ~18 µM ATP respectively. Further studies indicated that 50 µM was the lowest ATP concentration at which a robust day-to-day assay signal was observed (e.g. signal: 8000, 2% CV). ATP levels below this (10 µM) resulted in a higher relative variation in assay signal (e.g.

signal: 2500, 10% CV). The final ATP concentration of the screening assay was defined as 50 µM to provide an signal window large enough to support any attrition during the transfer of the assay to automation.

Time Course of Screening Assay.

It is critical that a screening assay is performed within its period of linearity. To determine the length of the linear phase of the coupled assay, a time course was performed up to 75 minutes. The reaction was linear between 5 and 45 minutes. The 'lag' period observed is characteristic of this assay format and reflects the time required to accumulate detectable levels of reaction product. Based upon this study an incubation period of 45 minutes at room temperature was defined.

Finalised Conditions for B-RafV599E DELFIA Assay

The summary final screening conditions for the assay were as follows:

Enzyme Reaction:
   384 well glutathione-coated plate
   0.05 µl B-Raf lysate
   6.5 µg/ml GST-MKK1
   80 µg/ml GST-kdERK2
   50 µM ATP
   incubation at room temperature for 45 minutes.
   Final volume of 25 µl Detection Conditions:
   1:3000 anti-phosphoERK2 antibody
   1:1000 Eu-labelled anti-mouse antibody Automation Development and Quality Control Validation of Screening Batch Reagents Using the conditions described in above, assays were performed to compare the screening and assay development batches of B-Raf, MKK1 and ERK-2. In all cases the screening batch of reagents performed equivalently when compared to those used for assay development.

Mini-Runs of Automated B-RatV599E DELFIA Assay.

In preparation for the screen, an automated liquid handling strategy was designed for the assay. In order to test this system, 'mini-runs' of the automated B-Raf assay were performed using mock screening plates (i.e. no compound but containing standard control columns). The data derived from these experiments represents both a measure of the robustness of the biological assay as well as the accuracy and consistency of the automation processes involved.

In brief, each plate contained B-Raf kinase reactions in all wells of Columns 1-22 and columns 23-24 contained the control reactions. In order to define the quality of data generated by the automated assay, 4 plate mini-runs using this format were performed on two separate days. Within each 'mini run' one plate was used to define IC50 values for some predicted inhibitors of this assay. The inhibitors covered a range of modes of action: Staurosporine (ATP-competitive kinase inhibitor), SB203580 (ATP-competitive Raf inhibitor) and U0126 (non-ATP competitive MKK1 inhibitor).

The assay demonstrates good consistency, both within plates and between days. The data obtained show that the automated assay achieves the criteria defined for a 384-format in vitro HTS assay:
   Signal to background of at least 10:1
   Z' of >0.4
   Row and column CVs of <15%

The inhibitors employed further validate the assay by generating concentration-dependent inhibition of Raf/MKK1 activity. Of particular importance is the fact that standard inhibitors returned IC50 values within a 2-fold range on separate days. These data also indicate that these compounds would have been identified as hits when tested at ~30 µm (10 µg/ml) in this screening assay.

Finalised Protocol for Automated B-Raf V599E DELFIA
   Enzyme cocktail (final volume 12 µl):
   0.05 µl Raf lysate
   0.0325 µl GST-MKKI
   0.065 µl GST-k-dERK2

1. 3 µl test compound pre-plated in glutathione-coated 384 plate.
2. 12 µl Enzyme cocktail added by PlateMatePlus.
3. 10 µl ATP added by Asys.
4. Plate shaken at RT for 45 min.
5. Plate washed with 3×80 µl/well DELFIA Wash Buffer (DWB) using plate washer ELX405.
6. 25 µl of anti-phosphoERK2 added by Multidrop.
7. Plate shaken at RT for 1 h
8. Plate washed with 3×80 µl/well DWB.
9. 25 µl Eu-labelled anti-mouse antibody added by Multidrop.
10. Plate shaken for 30 minutes room temperature.
11. Plate washed with 3×80 µl/well DWB.
12. 25 µl DELFIA Enhancement Solution added by Multidrop.
13. Plate incubated at Room Temperature in the dark for 30 minutes.
14. Plate read in FUSION.

TABLE 2

This table shows the inhibition of growth of various cell lines with B-Raf mutations. The proportion of inhibition (as a percentage of the number of cells that do not incorporate BrdU) is shown in the last column.

| cell name | tissue | Ras Mutation | B-Raf mutation | Y13-259 S-phase | inhibition |
|---|---|---|---|---|---|
| SW620 | colorectal | onc | wt | inhibited | 92% |
| SK-Mel2 | melanoma | | wt | inhibited | 70% |
| HMV11-Riken | melanoma | | wt | inhibited | 100% |
| DLD1 | colorectal | K13Asp/wt | wt | inhibited | 40% |
| SW480 | colorectal | K12 | wt | inhibited | 57% |
| LS174T | colorectal | K12Asp/wt | wt | inhibited | 84% |
| JW2 | colorectal | K12 | wt | inhibited | 79% |
| CaCO2 | colorectal | wt | wt | inhibited | 60% |
| HCT-116 | colorectal | K13 Asp | wt | inhibited | 95% |
| colo741 | colorectal | | V599E | not | 0% |
| SK-MEL-28 | melanoma | b | V599E | not | 4% |
| WM-266-4/WM-115 | melanoma | b | V599D | not | 10% |
| A2058 | melanoma | | V599E | not | 0% |
| Malme | melanoma | | V599E | not | 0% |
| LS411N | colorectal | | V599E | not | 0%, 0% |

TABLE 2-continued

This table shows the inhibition of growth of various cell lines with B-Raf mutations. The proportion of inhibition (as a percentage of the number of cells that do not incorporate BrdU) is shown in the last column.

| cell name | tissue | Ras Mutation | B-Raf mutation | Y13-259 S-phase | inhibition |
|---|---|---|---|---|---|
| HT29 | colorectal | wt | V599E | not | 15% |
| colo205 | colorectal | wt | V599E | not | ?3% |
| Mawi | colorectal | wt | V599E | not | 5% |
| NCI-H2087 | NSCLC cell line pair | onc | L596V | inhibited | 77% |

TABLE 3

This table shows the inhibition of cell growth in cells treated with the MEK inhibitor U0126.

| cell name | tissue | Ras Mutation | B-Raf mutation | U0 inhibit S | UO/ERK-inhib |
|---|---|---|---|---|---|
| SW620 | colorectal | onc | wt | 92% | |
| CHL | melanoma | | wt | 51% | >90% |
| colo741 | colorectal | | V599E | 76% | 90% |
| SK-MEL-28 | melanoma | b | V599E | 98% | >90% |
| WM-266-4/WM-115 | melanoma | b | V599D | >99% | >90% |
| A2058 | melanoma | | V599E | 68% | 80% |
| NCI-H2087 | NSCLC cell line pair | onc | L596V | 56% | >90% |
| Mawi | colorectal | wt | V599E | 80% | >90% |

TABLE 4

Inhibition of cell growth by BAY 43-9006.

| Cell line | IC50 μM |
|---|---|
| WM266.4 | 6.1 |
| Colo 829 | 5.1 |
| BE | 5.4 |

Cell lines were incubated in the presence of increasing levels of BAY 43-9006 and the levels of cell growth were determined by sulphorhodamine B staining. The $IC_{50}$ values were determined by non-linear regression analysis and are indicated.

TABLE 5

Cell cycle analysis.

| | Proportion of events (%) | | | | | |
|---|---|---|---|---|---|---|
| Cell line | untreated | U0126 | DMSO | SiRNA BRAF | SiRNA CRAF | SiRNA scrambled |
| Sub-G1 | 0.8 | 3.5 | 0.1 | 2.9 | 0.6 | 0.3 |
| G1 | 87.8 | 87.5 | 87.8 | 86.6 | 86.3 | 90.1 |
| S | 4.8 | 1.3 | 4.5 | 3.6 | 7.8 | 3.6 |
| G2/M | 6.7 | 7.8 | 7.5 | 7 | 5.4 | 6.1 |

WM-266.4 cells were treated with U0126, DMSO, siRNA to BRAF, siRNA to CRAF or the scrambled siRNA control. The cells were incubated for 96 hours and the cells were fixed and stained with propridium iodide for cell cycle analysis by FACS. The proportion of cells in each phase of the cell cycle is shown.

Computational Aspects of Detection

The detection of mutant B-Raf polypeptides and/or mutant B-raf nucleic acids can be automated to provide rapid massively parallel screening of sample populations. Computerised methods for mutation detection are known in the art, and will generally involve the combination of a sequencing device, or other device capable of detecting sequence variation in polypeptides or nucleic acids, a data processing unit and an output device which is capable of displaying the result in a form interpretable by a technician or physician.

In a preferred aspect, therefore, the invention provides an automated method for detecting a mutation at a target sequence position in a nucleic acid derived from a naturally-occurring primary human tumour encoding a B-Raf polypeptide, comprising:

sequencing a sample of an amplification product of the nucleic acid from the naturally-occurring primary human tumour to provide a sample data set specifying a plurality of measured base pair identification data in a target domain extending from a start sequence position to an end sequence position;

determining presence or absence of the mutation in the sample conditional on whether the measured base pair identification datum for the target sequence position corresponds to a reference base pair datum for the target sequence position; and generating an output indicating the presence or absence of the mutation in the sample as established by the determining step.

Methods for sequencing and for detection of mutations in sequences are set forth above and generally known in the art. The invention makes use of such methods in providing an apparatus for carrying out the process of the invention, which apparatus comprises:

a sequence reading device operable to determine the sequence of a sample of a nucleic acid to provide a sample data set specifying measured base pair identification data in a target domain extending from a start sequence position to an end sequence position; and a data analysis unit connected to receive the sample data set from the sequencing device and operable to determine presence or absence of the mutation in the sample conditional on whether the measured base pair identification datum for the target sequence position corresponds to a reference base pair datum for the target sequence position.

Suitable sequence reading devices include automated sequencers, RFLP-analysers and mobility shift analysis apparata. Advantageously, the sequence of an amplification product of the target nucleic acid is analysed, and the apparatus moreover includes an amplification device such as a PCR machine.

Preferably, the apparatus also comprises an output device operable to generate an output indicating the presence or absence of the mutation in the sample determined by the data analysis unit. For example, the output device can comprise at least one of: a graphical user interface; an audible user interface; a printer; a computer readable storage medium; and a computer interpretable carrier medium.

The invention can moreover be configured to detect the mutant B-Raf protein itself. Thus, in a further aspect, the invention relates to an automated method for detecting a single amino acid mutation in a B-Raf polypeptide from a naturally-occurring primary human tumour, comprising:

applying a marker to one or more target amino acids in a sample of the B-Raf polypeptide;

reading the sample after applying the marker to determine presence or absence of the marker in the sample, thereby to indicate presence or absence of the single amino acid mutation in the sample; and generating an output indicating the presence or absence of the single amino acid mutation in the sample as determined by the reading step.

The marker preferably comprises a ligand that binds differentially to a wild-type B-Raf polypeptide without single amino acid mutation and to a mutant B-Raf polypeptide with the mutation. Preferential binding to either form of B-Raf is possible in the context of the invention.

The invention moreover provides an apparatus for detecting an amino acid mutation in a B-Raf polypeptide, comprising:

a protein marking device loaded with a marker and operable to apply a marker to one or more target amino acids in a sample of the B-Raf polypeptide; and a marker reading device operable to determine presence or absence of the marker in the sample, thereby to indicate presence or absence of the single amino acid mutation in the sample.

The marker used can be an antibody, and the protein marking device can be configured to implement an ELISA process.

Advantageously, the protein marking device comprises a microarrayer which is preferably configured to read the sample optically.

Preferably, the apparatus comprises an output device operable to generate an output indicating the presence or absence of the single amino acid mutation in the sample as determined by the marker reading device. Suitable output devices comprises at least one of: a graphical user interface; an audible user interface; a printer; a computer readable storage medium; and a computer interpretable carrier medium.

USES OF THE INVENTION

The present invention provides novel mutants of B-Raf polypeptides which are useful in the detection of neoplastic conditions, and the determination of prognoses for subjects suffering from such conditions. In general, the presence of a mutation in B-Raf as described herein is associated with the presence of neoplasia.

In one aspect, the present invention provides a method for identifying cancerous cells or tissue (such as malignant melanoma, colorectal cancer, breast cancer or NSCLC), or of identifying cells or tissue which are predisposed to developing a neoplastic phenotype, comprising: amplifying at least part of a B-raf gene of the cells or tissue; analysing the amplification product to detect a mutation in the B-raf gene as described herein; wherein a cell or tissue having one or more B-raf mutations is categorised as being cancerous or being at an increased risk of developing a cancerous condition. Suitable amplification means include PCR and cloning.

In another embodiment, the present invention relates to a method for determining a prognosis in a subject suffering from cancer (such as malignant melanoma, colorectal cancer, breast cancer or NSCLC). The method comprises: amplifying the region of the B-raf gene as described above; analysing the amplification products for evidence of mutation as described above; and classifying a subject having no mutations in the B-raf gene as being less likely to suffer a relapse of the disease after therapy and/or surgery, or having an increased chance of survival than a patient having one or more mutations in the region.

The techniques of the invention can also be employed to determine the course of therapy to which a subject should be exposed, on the basis of the prognosis as set forth above; a subject having a poor prognosis is advantageously handled using a more aggressive therapy that a subject having a good prognosis.

The techniques according to the invention can be automated, as required for rapid screening of samples for the identification of potentially cancerous conditions. Generally, an automated process will comprise automated amplification of nucleic acid from tissue or cell samples, detection of mutations in amplified nucleic acid, such as by fluorescent detection, and/or displaying the presence of mutations. Exemplary automated embodiments are described above.

The identification of mutant B-Raf according to the invention can thus be used for diagnostic purposes to detect, diagnose, or monitor diseases, disorders, and/or conditions associated with the expression of mutant B-Raf. In particular, the invention is concerned with the detection, diagnosis and/or monitoring of cancers associated with mutant B-Raf as set forth herein.

The invention provides a diagnostic assay for diagnosing cancer, comprising (a), assaying the expression of mutant B-Raf in cells or body fluid of an individual using one or more antibodies specific to the B-Raf mutant as defined herein. The presence of mutant B-raf transcript in biopsy tissue from an individual can indicate a predisposition for the development of the disease, or can provide a means for detecting the disease prior to the appearance of actual clinical symptoms. A more definitive diagnosis of this type allows health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., (1985) J. Cell. Biol. 101:976-985; Jalkanen, et al., (1987) J. Cell. Biol. 105:3087-3096). Other antibody-based methods useful for detecting protein gene expression include inmuunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulphur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

Moreover, mutations in B-raf can be detected by analysis of nucleic acids, as set forth herein. For example, the presence of mutations can be detected by sequencing, or by SCCP analysis.

The present invention moreover provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody can be conjugated to a detectable substrate such as a fluorescent compound, an enzymatic substrate, a radioactive compound or a luminescent compound, or a second antibody which recognises the first antibody can be conjugated to a detectable substrate).

In another specific embodiment of the present invention, the kit is a diagnostic kit for use in screening serum containing antibodies specific for mutant B-Raf polypeptides as described herein. Such a kit can include a control antibody that does not react with the mutant B-Raf polypeptide. Such a kit can include a substantially isolated polypeptide antigen comprising an epitope which is specifically imnmunoreactive with at least one anti-B-Raf antibody. Further, such a kit includes means for detecting the binding of said antibody to the antigen (e.g., the antibody can be conjugated to a fluorescent compound such as fluorescein or rhodamine which can be detected by flow cytometry). In specific embodiments, the kit can include a recombinantly produced or chemically synthesised polypeptide antigen. The polypeptide antigen of the kit can also be attached to a solid support.

In an additional embodiment, the invention includes a diagnostic kit for use in screening serum containing antigens of the mutant B-Raf polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody can be a monoclonal antibody. The detecting means of the kit can include a second, labelled monoclonal antibody. Alternatively, or in addition, the detecting means can include a labelled, competing antigen.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the following claims.

We claim:

1. An isolated nucleic acid that hybridizes under stringent hybridization conditions to SEQ ID NO: 2,
   wherein the nucleic acid is the complement of a polynucleotide that encodes a variant B-Raf polypeptide having kinase activity and comprising Glu or Asp at the position corresponding to position 599 of SEQ ID NO: 1,
   wherein said stringent hybridization conditions comprise an overnight incubation at 42° C. in a solution comprising 50% formamide, 5X SSC (750 mM NaCl, 75 mM trisodium citrate), 50 mM sodium phosphate (pH 7.6), 5X Denhardt's solution, 10% dextran sulphate, and 20 pg/ml denatured, sheared salmon sperm DNA, followed by washing the filters in 0.1X SSC at 65° C.

2. An isolated nucleic acid which comprises a polynucleotide encoding a variant B-Raf polypeptide having at least 95% identity to SEQ ID NO: 1, wherein the polypeptide comprises a Glu or Asp at the position corresponding to position 599 of SEQ ID NO: 1 and has kinase activity.

3. The complement of the isolated nucleic acid of claim 2.

* * * * *